United States Patent
Nielsen et al.

(10) Patent No.: US 9,018,161 B2
(45) Date of Patent: Apr. 28, 2015

(54) PROTEASE RESISTANT INSULIN ANALOGUES

(75) Inventors: Peter Kresten Nielsen, Holte (DK); Frantisek Hubalek, Copenhagen Ø (DK); Inger Lautrup-Larsen, Virum (DK); Svend Ludvigsen, Lynge (DK); Ulla Ribel-Madsen, Virum (DK); Per Balschmidt, Hørsholm (DK); Per Nørgaard, Humlebæk (DK); Svend Havelund, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 1029 days.

(21) Appl. No.: 12/442,190

(22) PCT Filed: Sep. 20, 2007

(86) PCT No.: PCT/EP2007/059990
§ 371 (c)(1),
(2), (4) Date: Jul. 21, 2009

(87) PCT Pub. No.: WO2008/034881
PCT Pub. Date: Mar. 27, 2008

(65) Prior Publication Data
US 2010/0009898 A1    Jan. 14, 2010

Related U.S. Application Data

(60) Provisional application No. 60/847,500, filed on Sep. 27, 2006.

(30) Foreign Application Priority Data

Sep. 22, 2006  (EP) .................................... 06121113

(51) Int. Cl.
*A61K 38/28* (2006.01)
*C07K 14/62* (2006.01)
*A61K 38/00* (2006.01)

(52) U.S. Cl.
CPC ............... *C07K 14/62* (2013.01); *A61K 38/00* (2013.01)

(58) Field of Classification Search
CPC ............................. A61K 38/28; C07K 14/62
See application file for complete search history.

(56) References Cited

U.S. PATENT DOCUMENTS

| | | | |
|---|---|---|---|
| 2,832,685 A | 4/1958 | Scott | |
| 3,528,960 A | 9/1970 | Haas | |
| 3,719,655 A | 3/1973 | Jackson et al. | |
| 3,869,437 A | 3/1975 | Lindsay et al. | |
| 3,950,517 A | 4/1976 | Lindsay et al. | |
| 4,033,941 A | 7/1977 | Stilz et al. | |
| 4,179,337 A | 12/1979 | Davis et al. | |
| 5,149,777 A | 9/1992 | Hansen et al. | |
| 5,179,189 A | 1/1993 | Domb et al. | |
| 5,359,030 A | 10/1994 | Ekwuribe | |
| 5,478,575 A | 12/1995 | Miyazaki et al. | |
| 5,506,202 A | 4/1996 | Vertesy et al. | |
| 5,506,203 A | 4/1996 | Backstrom et al. | |
| 5,597,796 A * | 1/1997 | Brange ........................ 514/6.2 |
| 5,716,927 A | 2/1998 | Balschmidt et al. | |
| 5,898,067 A | 4/1999 | Balschmidt et al. | |
| 5,922,675 A | 7/1999 | Baker et al. | |
| 6,221,837 B1 | 4/2001 | Ertl et al. | |
| 6,251,856 B1 | 6/2001 | Markussen et al. | |
| 6,475,795 B1 | 11/2002 | Turley et al. | |
| 6,500,645 B1 | 12/2002 | Kjeldsen et al. | |
| 6,746,853 B1 * | 6/2004 | Dahiyat et al. ............... 435/69.1 |
| 6,770,625 B2 | 8/2004 | Soltero et al. | |
| 6,867,183 B2 | 3/2005 | Soltero et al. | |
| 6,869,930 B1 | 3/2005 | Havelund et al. | |
| 7,030,082 B2 | 4/2006 | Soltero et al. | |
| 7,030,083 B2 | 4/2006 | Schreiner et al. | |
| 2002/0045731 A1 | 4/2002 | Schaffer et al. | |
| 2002/0198140 A1 | 12/2002 | Havelund | |
| 2003/0027748 A1 | 2/2003 | Ekwuribe et al. | |
| 2003/0035775 A1 | 2/2003 | Klibanov | |
| 2003/0083232 A1 | 5/2003 | Soltero et al. | |
| 2003/0104981 A1 | 6/2003 | Mandic | |
| 2003/0134294 A1 | 7/2003 | Sandford et al. | |
| 2003/0166508 A1 | 9/2003 | Zhang | |
| 2004/0038867 A1 | 2/2004 | Still et al. | |
| 2004/0097410 A1 | 5/2004 | Zheng et al. | |
| 2004/0198949 A1 | 10/2004 | Ekwuribe et al. | |
| 2004/0254119 A1 | 12/2004 | West et al. | |
| 2005/0276843 A1 | 12/2005 | Quay et al. | |

(Continued)

FOREIGN PATENT DOCUMENTS

CN     1390854 A    1/2003
EP      214826      3/1987

(Continued)

OTHER PUBLICATIONS

Kaarsholm et al. ("Engineering Stability of the Insulin Monomer Fold with Application to Structure-Activity Relationships," Biochemistry, 1993, 32, 10773-8).*

Brange et al. ("Design of Novel Insulins with Changed Self-Association and Ligand Binding Properties,"GBF Monographs, 1989, 12, 139-144).*

Seabright et al. ("The characterization of endosomal insulin degradation intermediates and their sequence of production," Biochem. J. (1996) 320, 947-956).*

Bajaj et al. ("Primary structure, conformation and biological properties of a hystricomorph rodent insulin," Biochem. J. (1986) 238, 345-351).*

(Continued)

*Primary Examiner* — Christina Bradley
(74) *Attorney, Agent, or Firm* — Jianjie Hu

(57) ABSTRACT

The present invention relates to novel insulin analogues exhibiting resistance towards protease, wherein at least two amino acids are substituted and/or deleted relative to the parent insulin molecule. A method for the preparation of such insulin analogues, insulin preparations containing the insulin analogues of the invention and a method of treating diabetes mellitus using these insulin analogues is also provided.

31 Claims, 2 Drawing Sheets

(56) References Cited

U.S. PATENT DOCUMENTS

| | | |
|---|---|---|
| 2006/0019874 A1 | 1/2006 | Radhakrishnan et al. |
| 2006/0183668 A1 | 8/2006 | Jonassen et al. |
| 2008/0076705 A1 | 3/2008 | Kodra et al. |
| 2008/0171695 A1 | 7/2008 | Garibay et al. |
| 2011/0105720 A1 | 5/2011 | Madsen et al. |

FOREIGN PATENT DOCUMENTS

| | | |
|---|---|---|
| EP | 265213 A2 | 4/1988 |
| EP | 376156 A2 | 7/1990 |
| EP | 511600 A2 | 11/1992 |
| EP | 544466 | 6/1993 |
| EP | 712861 A2 | 5/1996 |
| EP | 712862 A2 | 5/1996 |
| EP | 837072 A2 | 4/1998 |
| EP | 925792 A2 | 6/1999 |
| EP | 1121144 A1 | 4/2000 |
| EP | 1002547 A1 | 5/2000 |
| EP | 0894095 | 5/2003 |
| GB | 1492997 A | 11/1977 |
| JP | 57-067548 A | 4/1982 |
| JP | 1254699 A | 10/1989 |
| JP | H03-506023 A | 12/1991 |
| JP | H09502867 A | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2001-521004 A | 11/2001 |
| JP | 2001-521006 A | 11/2001 |
| JP | 2001-521904 A | 11/2001 |
| JP | 2002-308899 A | 10/2002 |
| JP | 2002-543092 A | 12/2002 |
| JP | 2003-518917 A | 6/2003 |
| RU | 2146139 C1 | 3/2000 |
| WO | 8910937 A1 | 11/1989 |
| WO | 90/01038 A1 | 2/1990 |
| WO | 90/12814 A1 | 11/1990 |
| WO | 91/12817 A1 | 9/1991 |
| WO | 92/00321 A1 | 1/1992 |
| WO | 92/00322 A1 | 1/1992 |
| WO | 92/01476 A1 | 2/1992 |
| WO | 92/12999 A1 | 8/1992 |
| WO | 94/08599 A1 | 4/1994 |
| WO | 95/07931 A1 | 3/1995 |
| WO | 95/13795 A1 | 5/1995 |
| WO | 95/24183 A1 | 9/1995 |
| WO | 96/15803 A1 | 5/1996 |
| WO | 96/29344 | 9/1996 |
| WO | 96/37215 A1 | 11/1996 |
| WO | 97/31022 A1 | 8/1997 |
| WO | 98/02460 A1 | 1/1998 |
| WO | WO 98/01473 | 1/1998 |
| WO | 99/21888 A1 | 5/1999 |
| WO | 99/24071 A1 | 5/1999 |
| WO | 99/65941 A1 | 12/1999 |
| WO | 00/00176 A1 | 1/2000 |
| WO | 00/10541 A1 | 3/2000 |
| WO | 00/23098 A1 | 4/2000 |
| WO | 00/43034 A2 | 7/2000 |
| WO | 0042993 A2 | 7/2000 |
| WO | 00/61178 A1 | 10/2000 |
| WO | 00/69901 A2 | 11/2000 |
| WO | 00/78302 A1 | 12/2000 |
| WO | 02/094200 A2 | 11/2002 |
| WO | 02098232 | 12/2002 |
| WO | 02098446 A1 | 12/2002 |
| WO | 03/013573 | 2/2003 |
| WO | 03/022208 A2 | 3/2003 |
| WO | 03/022996 A2 | 3/2003 |
| WO | 03/047493 A2 | 6/2003 |
| WO | 03/048195 A2 | 6/2003 |
| WO | 03/053339 A2 | 7/2003 |
| WO | 03/094951 A1 | 11/2003 |
| WO | 03/094956 A1 | 11/2003 |
| WO | 2004/105790 A1 | 12/2004 |
| WO | 2005/005477 A2 | 1/2005 |
| WO | 2005/012346 A1 | 2/2005 |
| WO | 2005/012347 A2 | 2/2005 |
| WO | 2005/016312 A1 | 2/2005 |
| WO | 2005/047508 A1 | 5/2005 |
| WO | 2005/049061 A2 | 6/2005 |
| WO | 2005/055976 A2 | 6/2005 |
| WO | 2005/058961 A2 | 6/2005 |
| WO | 2005/092301 A1 | 10/2005 |
| WO | 2006/023943 A1 | 3/2006 |
| WO | 2006/079641 A2 | 8/2006 |
| WO | 2006/082204 A1 | 8/2006 |
| WO | 2006/082205 A1 | 8/2006 |
| WO | 2006/097521 A1 | 9/2006 |
| WO | 2007/006320 A1 | 1/2007 |
| WO | 2007/041481 A1 | 4/2007 |
| WO | 2007/047948 A2 | 4/2007 |
| WO | 2007/074133 A2 | 7/2007 |
| WO | WO 2007/081824 | 7/2007 |
| WO | 2007/096332 A1 | 8/2007 |
| WO | 2007/096431 A1 | 8/2007 |
| WO | 2007/104737 A1 | 9/2007 |
| WO | 2007/128815 A1 | 11/2007 |
| WO | 2007/128817 A2 | 11/2007 |
| WO | 2008/015099 A2 | 2/2008 |
| WO | 2008/034881 A1 | 3/2008 |
| WO | 2008/132229 A2 | 11/2008 |
| WO | 2008/145730 A1 | 12/2008 |
| WO | 2009/010428 A1 | 1/2009 |
| WO | 2009/022005 A1 | 2/2009 |
| WO | 2009/022006 A1 | 2/2009 |
| WO | 2009/112583 A2 | 9/2009 |
| WO | 2009/115469 A1 | 9/2009 |

OTHER PUBLICATIONS

Schilling, R.J., et al, Pharmaceutical Research, 1991, vol. 8 (6), pp. 721-727, "Degradation of Insulin by Trypsin and Alpha-Chymotrypsin".

Bennett, R.G., et al, Journal of Endocrinology, 2003, vol. 177, pp. 399-405, "Insulin inhibition of the proteasome is dependent on degradation of insulin by insulin-degrading enzyme".

Spoden M et al. International Journal of Peptide and Protein. "Structure-Function Relationships of DES-(B26-B30)-Insulin." 1995. vol. 46(3-4). pp. 221-227.

Chen, Y et al. Journal of Biological Chemistry. "In Vitro Refolding/Unfolding Pathways of Amphioxus Insulin-Like Peptide Implications for Folding Behavior of Insulin Family Proteins." 2004. vol. 279(53). pp. 55224-55233.

Smith, L.E, "Accession: P01337 1 [gi: 32172038] & Accession: P01337 2 [gi: 32172039], Definition: [Segment 1 of 2] Insulin-1 & [Segment 2 of 2] Insulin-1", NCBI Entrez Protein [online]; Mar. 21, 2006 uploaded, NCBI, [retrieved on Sep. 11, 2013], Retrieved from the internet:http://www.ncbi.nlm.nih.gov/protein/32172037?sat=34 &satkey=10044352.

Aminlari et al., 1977, "Protein Dispersibility of Spray-Dried Whole Soybean Milk Base: Effect of Processing Variables," Journal of Food Science 42(4):985-988.

Bekerman et al., 2004, "Cyclosporin Nanoparticulate Liposheres for Oral Administration," Journal of Pharmaceutical Sciences 93(5):1264-1270.

Bennett et al., 2003, "Insulin Inhibition of the Proteasome is Dependent on Degradation of Insulin by Insulin-Degrading Enzyme," Journal of Endocrinology 177:399-405.

Bhatnagar et al., 2006, "Molecular Variants and Derivatives of Insulin for Improved Glycemic Control in Diabetes," Progress in Biophysics and Molecular Biology 91(3):199-228.

Chin et al., 1994, "Communication to the Editor: On Protein Solubility in Organic Solvents," Biotechnology and Bioengineering 44:140-145.

Foster et al., 1995, "Powder Characteristics of Proteins Spray-Dried From Different Spray-Driers," Drug Development and Industrial Pharmacy 21(15):1705-1723.

Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3):175-181.

(56) References Cited

OTHER PUBLICATIONS

Hashimoto et al., 1989, "Synthesis of Palmitoyl Derivatives of Insulin and Their Biological Activities" Pharmaceutical Research 6(2):171-176.
Havelund et al., 2004, "The Mechanism of Protraction of Insulin Detemir, a Long-Acting, Acylated Analog of Human Insulin" Pharmaceutical Research 21(8):1498-1504.
Hinds et al., 2000, "Synthesis and Characterization of Poly(Ethylene Glycol)-Insulin Conjugates," Bioconjugate Chemistry 11(2):195-201.
Hinds et al., 2002, "Effects of Peg Conjugation on Insulin Properties," Advanced Drug Delivery Reviews 54 (4):505-530.
Iwamoto, 2000, "New Insulin Formulation," Annual Review Endocrine Metabolism pp. 46-53.
Jonassen et al., 2006, "Synthesis of Palmitoyl Derivatives of Insulin and Their Biological Activities," Pharmaceutical Research 23(1):49-55.
Kochendoerfer et al., 2003, "Design and Chemical Synthesis of a Homogenous Polymer-Modified Erythropoiesis Protein," Science 299:884-887.
Kurtz et al., 1983, "Circulating IgG Antibody to Protamine in Patients Treated with Protamine-Insulins," Diabetologia 25(2):322-324.
Markussen et al., 1987, "Soluble, Prolonged-Acting Insulin Derivatives. I. Degree of Protraction, Crystallizability of Insulins Substituted in the . . . " Protein Engineering 1(3):205-213.
Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2 (2):157-166.
Muranishi et al., 1992, "Trials of Lipid Modification of Peptide Hormones for Intestinal Delivery," Journal of Controlled Release 19:179-188.
Samuel et al., 1978, "Studies on the Immunogenicity of Protamines in Humans Andexperimental Animals by Means of a Micro-Complement Fixation Test," Clinical Experminemtal Immunology 33:252-260.
Schlichtkrull et al., 1956, "Insulin Crystals," Acta Chemica Scandinavica 10(9):1455-1458.
Toorisaka et al., 2004, "Emulsion-Based Drug Delivery Systems," Membrane 29(2):98-104 Abstract.
Uchio et al., 1999, "Site-Specific Insulin Conjugates With Enhanced Stability and Extended Action Profile," Advanced Drug Delivery Reviews 35:289-306.
Whittingham et al., 2004, "Crystallographic and Solution . . . " Biochemistry 43:5987-5995.
L. Schaffer et al ,A novel high-affinity peptide antagonist to the insulin receptor.Journal: Biochemical and Biophysical Research Communications, Year 2008, vol. 376 , pp. 380-383.
Riebel, U. et al,Equivalent In Vivo Biological Activity of Insulin Analogues and Human Insulin Despite Different In Vitro Potencies, Journal :Diabetes, Year 1990,vol. 39, pp. 1033-1039.
Hinds, K D et al. Advanced Drugs Delivery Reviews. "Effects of Peg Conjugation on Insulin Properties." 2002. vol. 54. pp. 505-530.
Chu Ying-Chi et al. Journal of Protein Chemistry. "The A14 Position of Insulin Tolesrates Considerable Structural Alterations With Modest Effects on the Biological Behavior of the Hormone." 1992. vol. 11(5). pp. 571-577.
Database Geneseq [Online] May 7, 1992, "Modified human proinsulin with Gln A13 and Asp B17.", retrieved from EBI accession No. GSP:AAR20702 Database accession No. AAR20702.
Definition of hydrophobic and hydrophilic, Amino Acids, NJMS Department of Biochemistry and Molecular Biology. (http://njms2.umdnj.edu/biochweb/education/bioweb/PreK/AminoAcids.htm).
Hydrophobic Amino Acids, Molecular Cell Biology 6th edition (2008, W.H. Freeman and company) http://www.bio.miami.edu/tom/courses/protected/MCB6/ch02/2-14_part_1.jpg.
L. Schaffer et al, Assembly of high-affinity insulin receptor agonists and antagonists from peptide building blocks, Journal :Proceedings of the National Academy of Sciences of the United States of America, Year 2003, vol. 100, pp. 4435-4439.

Ying-Chi Chu et al. "The A14 Position of Insulin Tolerates Cinsiderable Structural Alterations with Modest Effects on the Biological Behavior of the Hormone," Journal of Protein Chemistry, 1992, vol. 11, pp. 571-577.
Yip, C.C. et al. "Structure and function of Insulin: Preparation and Biological Activity of Guinea Pig DES-B-ASP30, DES-A-ASN21-Insulin." Canadian Journal of Biochemistry, 1976, vol. 54 pp. 866-871.
Stentz, F.B. et al., "Identification of Insulin Intermediates and Sites of Cleavage of Native Insulin by Insulin Protease from Human Fibroblasts," Journal of Biological Chemistry, 1989, vol. 264, No. 34 pp. 20275-20282.
Baker et al., Philosophical Transactions of the Royal Society of London, 1988, vol. 319, p. 369-456.
Ward et al., Bioessays, 2009, vol. 31, pp. 422-434.
Seino et al., Biochemical and Biophysical Research Communications, 1989, vol. 159, pp. 312-316.
Moller et al., Molecular Endocrinology, 1989, vol. 3, No. 8, pp. 1263-1269.
Mosthaf et al., The EMBO Journal, 1990, vol. 9, pp. 2409-2413.
Yamaguchi et al., Endocrinology, 1991, vol. 129, No. 4, pp. 2058-2066.
Yamaguchi et al., Endocrinology, 1993, vol. 132, No. 3, pp. 1132-1138.
Blundell et al., Advances in Protein Chemistry, 1972, vol. 26, pp. 279-402.
Pullen et al., Nature, 1976, vol. 259, pp. 369-373.
Nakagawa et al., Journal of Biological Chemistry, 1987, vol. 262, No. 25, pp. 12054-12058.
Mirmira et al., The Journal of Biological Chemistry, 1991, vol. 266, No. 3, pp. 1428-1436.
Xu et al., Biochemistry, 2004, vol. 43, pp. 8356-8372.
De Meyts et al., Biochemical and Biophysical Research Communications, 1973, vol. 55, pp. 154-161.
Kurose et al., Journal of Biological Chemistry, 1994, vol. 269, No. 46, pp. 29190-29197.
Shoelson et al., Journal of Biological Chemistry, 1993, vol. 268, No. 6, pp. 4085-4091.
Zakova et al., Biochemistry, 2008, vol. 47, pp. 5858-5868.
Fischer et al., Biological Chemistry, 1985, vol. 366, pp. 521-525.
Hua et al., Nature, 1991, vol. 354, pp. 238-241.
Ludvigsen et al., Jouronal of Molecular Biology, 1998, vol. 279, pp. 1-7.
Nakagawa et al., Biochemistry, 1992, vol. 31, pp. 3204-3214.
Markussen et al., International Journal of Peptide and Protein Research, 1985, vol. 26, No. 1, pp. 70-77.
Shoelson et al., Nature, 1983, vol. 302, pp. 540-543.
Glendorf et al., Biochemistry, 2008, vol. 47, pp. 4743-4751.
Soos et al., Biochemical Journal, 1986, vol. 235, No. 1, pp. 199-208.
Slaaby et al., Journal of Biological Chemistry, 2006, vol. 281, No. 36, pp. 25869-25874.
Volund, Biometrics, 1978, vol. 34, pp. 357-365.
Kabsch, Journal of Applied Crystallogrpahy, 1993, vol. 26, pp. 795-800.
Vagin et al., Journal of Applied Crystallography, 1997, vol. 30, pp. 1022-1025.
Murshudov, Acta Crystallographica, 1997, vol. 53, pp. 240-255.
Emsley et al., Acta Crystallographica, 2004, vol. 60, pp. 2126-2132.
Kjeldsen et al., Biotechnology and Genetic Engineering Reviews, 2001, vol. 18, pp. 89-121.
Schaffer, European Journal of Biochemistry, 1994, vol. 221, pp. 1127-1132.
Wells, Biochemistry, 1990, vol. 29, vol. 37, pp. 8509-8517.
Kaarsholm et al., Biochemistry, 1993, vol. 32, pp. 10773-10778.
Kristensen et al., Journal of Biological Chemistry, 2002, vol. 277, No. 21, pp. 18340-18345.
Mynarcik et al., Journal of Biological Chemistry, 1996, vol. 271, No. 5, pp. 2439-2442.
Whittaker, Journal of Biological Chemistry, 2005, vol. 280, No. 22, pp. 20932-20936.

(56) References Cited

OTHER PUBLICATIONS

Whittaker et al., Journal of Biological Chemistry, 2002, vol. 277, No. 49, pp. 47380-47384.

Frasca et al., Molecular and Cellular Biology, 1999, vol. 19, No. 5, pp. 3278-3288.

Kjeldsen et al., Proceedings of the National Academy of Sciences of the USA, 1991, vol. 88, No. 10, pp. 4404-4408.

* cited by examiner

PROTEASE RESISTANT INSULIN ANALOGUES

CROSS-REFERENCE TO RELATED APPLICATIONS

This application is a 35 U.S.C. §371 national stage application of International Patent Application PCT/EP2007/059990 (published as WO 2008/034881), filed Sep. 20, 2007, which claimed priority of European Patent Application EP 06121113.2, filed Sep. 22, 2006; this application further claims priority under 35 U.S.C. §119 of U.S. Provisional Application 60/847,500, filed Sep. 27, 2006.

FIELD OF THE INVENTION

The present invention relates to novel insulin analogues exhibiting resistance towards protease, a method for the preparation of such insulin analogues, insulin preparations containing the insulin analogues of the invention and a method of treating diabetes mellitus using these insulin analogues.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Mar. 16, 2009. The Sequence Listing is made up of 6 kilobytes, and the information contained in the attached "SEQUENCE LISTING" is identical to the information in the specification as originally filed. No new matter is added.

BACKGROUND OF THE INVENTION

The oral route is by far the most widely used route for drug administration and is in general very well accepted by patients, especially for chronic therapies. Administration of therapeutic peptides or proteins is however often limited to parenteral routes rather than the preferred oral administration due to several barriers such as enzymatic degradation in the gastrointestinal (GI) tract, drug efflux pumps, insufficient and variable absorption from the intestinal mucosa, as well as first pass metabolism in the liver. Human insulin is degraded by various digestive enzymes found in the stomach (pepsin), in the intestinal lumen (chymotrypsin, trypsin, elastase, carboxypeptidases, etc.) and in mucosal surfaces of the GI tract (aminopeptidases, carboxypeptidases, enteropeptidases, dipeptidyl peptidases, endopeptidases, etc.).

This is unfortunate because many peptides and many proteins have proven clinically effective and could have more widespread use if easy to administer and acceptable to recipients.

Diabetes mellitus is a metabolic disorder in which the ability to utilize glucose is partly or completely lost. About 5% of all people suffer from diabetes and the disorder approaches epidemic proportions. Since the introduction of insulin in the 1920's, continuous efforts have been made to improve the treatment of diabetes mellitus. Since people suffering from diabetes are subject to chronic treatment over several decades, there is a major need for safe, convenient and life quality improving insulin formulations.

In the treatment of diabetes mellitus, many varieties of insulin formulations have been suggested and used, such as regular insulin, isophane insulin (designated NPH), insulin zinc suspensions (such as Semilente®, Lente®, and Ultralente®), and biphasic isophane insulin. Some of the commercial available insulin formulations are characterized by a fast onset of action and other formulations have a relatively slow onset but show a more or less prolonged action. Fast-acting insulin formulations are usually solutions of insulin, while retarded acting insulin formulations can be suspensions containing insulin in crystalline and/or amorphous form precipitated by addition of zinc salts alone or by addition of protamine or by a combination of both.

Human insulin consists of two polypeptide chains, the A and B chains which contain 21 and 30 amino acid residues, respectively. The A and B chains are interconnected by two disulphide bridges. Insulin from most other species is similar, but may contain amino acid substitutions in some positions. Within the last decade a number of human insulin analogues have been developed. They are designed for particular profiles of action, i.e. fast acting or prolonged action. Commercially available products comprising such insulin analogues include Levemir®, NovoRapid®, Humalog®, Apidra® and Lantus®.

Normally, insulin formulations are administered by subcutaneous injection.

However, administration by the oral route would be advantageous due to patient compliance, safety and convenience.

Oral administration of protein drugs such as insulin often results in very low bioavailability due to enzymatic and absorption barriers. The general approach for peptide and protein delivery is parenteral administration which is invasive and inconvenient. Therefore non-invasive routes like oral delivery of protein based pharmaceuticals are increasingly investigated. Recent formulation designs for oral protein/peptide delivery include coformulations with protease inhibitors, permeation enhancers, polymer-based delivery systems and insulin conjugates. The latter includes hexyl-insulin-monoconjugate-2 (HIM2) (Nobex Cooperation and GSK), a human insulin analog with a PEG 7-hexyl group attached to B29. In for example U.S. Pat. Nos. 7,030,082, 6,867,183 and 6,770,625 oral HIM2 has been reported to have increased proteolytic stability and bioavailability compared to insulin.

SUMMARY OF THE INVENTION

In one embodiment of the invention an insulin analogue with enhanced proteolytic stability and retained biological insulin activity is provided.

In a further embodiment of the invention an insulin analogue is provided wherein at least two amino acids are substituted and/or deleted relative to the parent insulin molecule.

In yet a further embodiment of the invention an insulin analogue is provided wherein at least two hydrophobic amino acids have been substituted with hydrophilic amino acids relative to the parent insulin, wherein the substitutions are within or in close proximity to two or more protease cleavage sites of the parent insulin and wherein such insulin analogue optionally further comprises one or more additional mutations.

It is also an object of the invention to provide insulin analogues according to the invention wherein the A-chain of the insulin analogue comprises at least one mutation and the B-chain of the insulin analogue comprises at least one mutation relative to the parent insulin.

The present invention is also related to nucleic acid sequences which code for the prepropeptide of the claimed insulin analogues. In a further embodiment the present invention is related to vectors containing such nucleic acid sequences and host cells containing such nucleic acid sequences or vectors.

A process for obtaining an insulin analogue according to the invention and use thereof as a pharmaceutical is also provided.

DESCRIPTION OF THE INVENTION

Figure 1:
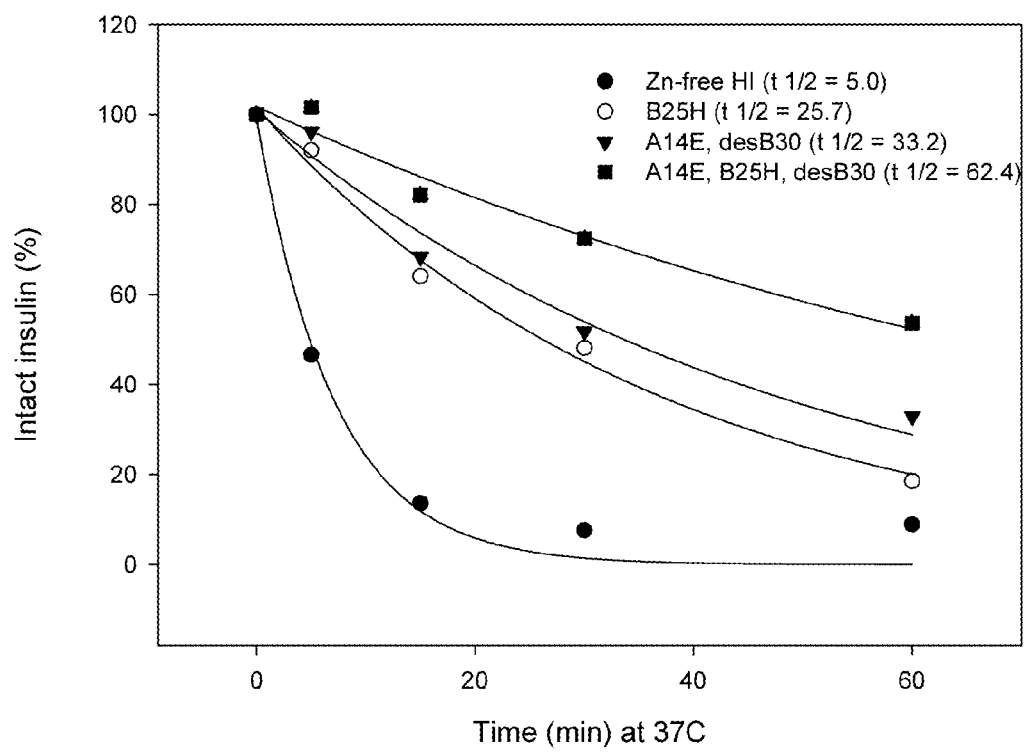
FIG. 1: Proteolytic stability of human insulin (HI) and insulin analogues towards chymotrypsin measured as percentage of intact insulin (analogue) at 37° C.
Figure 2:
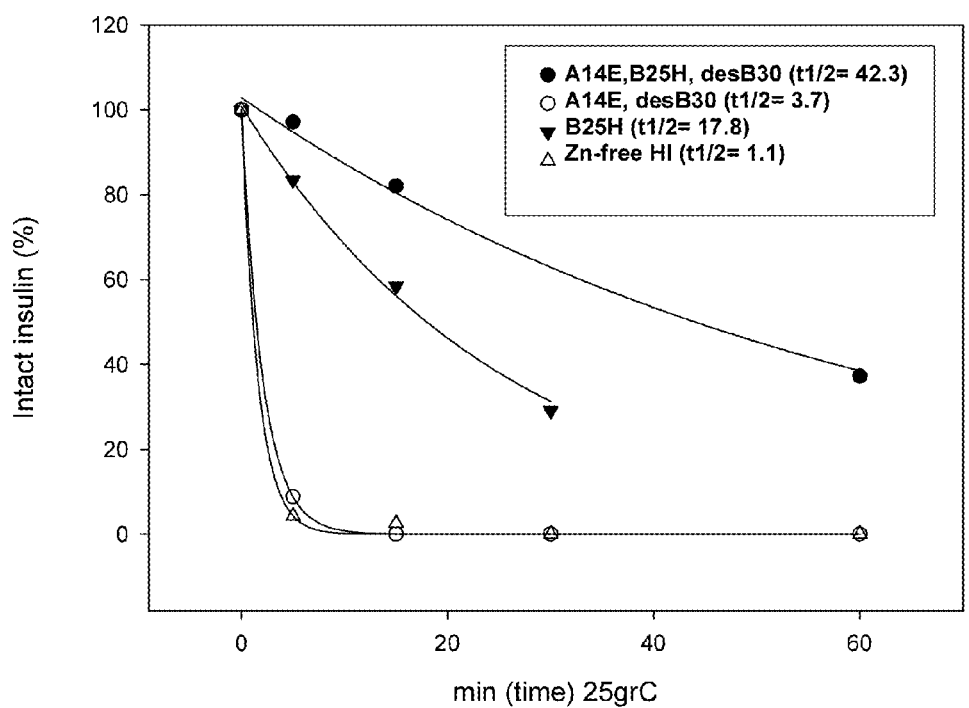
FIG. 2: Proteolytic stability of human insulin (HI) and insulin analogues towards pepsin measured as percentage of intact insulin (analogue) at 25° C.

An insulin analogue according to the invention is an insulin molecule having two or more mutations of the A and/or B amino acid chains relative to the parent insulin molecule.

It has been found that by substituting two or more hydrophobic amino acids within or in close proximity to two or more protease sites on an insulin with hydrophilic amino acids, an insulin analogue is obtained which is proteolytically stable compared to the parent insulin.

The following is a non-limiting list of embodiments, which is further described elsewhere herein:

Embodiment 1. An insulin analogue wherein at least two hydrophobic amino acids have been substituted with hydrophilic amino acids relative to the parent insulin, wherein the substitutions are within or in close proximity to two or more protease cleavage sites of the parent insulin and wherein such insulin analogue optionally further comprises one or more additional mutations.

Embodiment 2. An insulin analogue according to embodiment 1 wherein increased solubility relative to the parent insulin is obtained.

Embodiment 3. An insulin analogue according to any one of the embodiments 1-2 wherein the A-chain of the insulin analogue comprises at least one mutation and the B-chain of the insulin analogue comprises at least one mutation relative to the parent insulin.

Embodiment 4. An insulin analogue according to any one of the embodiments 1-3 wherein the insulin analogue further comprises at least one amino acid substitution in a protease site of a first modified insulin analogue, wherein said at least one amino acid substitution is such that at least one hydrophobic amino acid has been substituted with at least one hydrophilic amino acid.

Embodiment 5. An insulin analogue according to any of the embodiments 1-4 wherein
the amino acid in position A12 is Glu or Asp and/or the amino acid in position A13 is His, Asn, Glu or Asp and/or the amino acid in position A14 is Asn, Gln, Glu, Arg, Asp, Gly or His and/or the amino acid in position A15 is Glu or Asp; and
the amino acid in position B24 is His and or the amino acid in position B25 is His and/or the amino acid in position B26 is His, Gly, Asp or Thr and/or the amino acid in position B27 is His, Glu, Lys, Gly or Arg and/or the amino acid in position B28 is His, Gly or Asp; and
which optionally further comprises one or more additional mutations.

Embodiment 6. An insulin analogue according to any of the embodiments 1-5 wherein the amino acid in position A14 is Glu, Asp or His, the amino acid in position B25 is His and which optionally further comprises one or more additional mutations.

Embodiment 7. An insulin analogue according to any of the embodiments 1-6 wherein the amino acid in position A14 is Glu, Asp or His, the amino acid in position B25 is His and the amino acid in position B30 is deleted.

Embodiment 8. An insulin analogue according to any of the embodiments 1-6 wherein the amino acid in position A14 is Glu, Asp or His and the amino acid in position B25 is His.

Embodiment 9. An insulin analogue according to any of the embodiments 1-6 wherein the one or more additional mutations is selected from a group consisting of: A(−3)Gly, A(−2)Gly, A(−1)Pro, A(0)Pro, A8His, A18Gln, A18Gln, A21 Gln, A21Gly, B(−3)Gly, B(−2)Gly, B(−1)Pro, B(0)Pro, B1Glu, B1Gln, ro, B1Glu, B1Gln, B3Gln, B10Pro, B14Thr, B16Glu, B17Ser, B26Asp, DesB26, DesB27, B27Glu, B27Glu, B28Asp, desB28, desB29, desB30, B31Leu, B32Glu.

Embodiment 10. An insulin analogue according to any of the embodiments 1-6 or 9 wherein the additional mutation is desB30.

Embodiment 11. An insulin analogue according to any the embodiments 1-10 wherein A14 is Glu.

Embodiment 12. An insulin analogue according to any of the embodiments 1-11 which shows increased stability towards one or more protease enzymes relative to the parent protein.

Embodiment 13. An insulin analogue according to any of the embodiments 1-12 which shows increased stability towards two or more protease enzymes relative to the parent protein.

Embodiment 14. An insulin analogue according to any of the embodiments 1-13 wherein the parent insulin is selected from a group consisting of:
human insulin;
an insulin analogue of human insulin wherein the amino acid residue in position B28 is Pro, Asp, Lys, Leu, Val or Ala and the amino acid residue in position B29 is Lys or Pro and optionally the amino acid residue in position B30 is deleted;
des(B26-B30) human insulin, des(B27-B30) human insulin, des(B28-B30) human insulin, des(B29-B30) human insulin, des(B27) human insulin or des(B30) human insulin;
an insulin analogue of human insulin wherein the amino acid residue in position B3 is Lys and the amino acid residue in position B29 is Glu or Asp;
an insulin analogue of human insulin wherein the amino acid residue in position A21 is Gly and wherein the insulin analogue is further extended in the C-terminal with two Arg residues;
an insulin derivative wherein the amino acid residue in position B30 is substituted with a threonine methyl ester; and
an insulin derivative wherein to the Nε position of lysine in the position B29 of des(B30) human insulin a tetradecanoyl chain is attached.

Embodiment 15. An insulin analogue according to any of the embodiments 1-6, 9 or 11-14 wherein the one or more additional mutations are selected to enhance chemical stability of insulin.

Embodiment 16. An insulin analogue according to embodiment 15 wherein the one or more additional mutations are selected from a group consisting of: A18Gln, A21Gln, A21GLy and B3Gln.

Embodiment 17. An insulin analogue according to any of the embodiments 1-4 or 12-14 comprising an A-chain amino acid sequence of formula 1:

Formula (1)

(SEQ ID No: 1)
Xaa$_{A(-2)}$-Xaa$_{A(-1)}$-Xaa$_{A0}$-Gly-Ile-Val-Glu-Gln-Cys-

Cys-Xaa$_{A8}$-Ser-Ile-Cys-Xaa$_{A12}$-Xaa$_{A13}$-Xaa$_{A14}$-Xaa$_{A15}$-

Leu-Glu-Xaa$_{A18}$-Tyr-Cys-Xaa$_{A21}$-Xaa$_{A22}$ and a B-chain amino acid sequence of formula 2:

Formula (2)

(SEQ ID No: 2)
Xaa$_{B(-2)}$-Xaa$_{B(-1)}$-Xaa$_{B0}$-Xaa$_{B1}$-Xaa$_{B2}$-Xaa$_{B3}$-Xaa$_{B4}$-

His-Leu-Cys-Gly-Ser-Xaa$_{B10}$-Leu-Val-Glu-Ala-Leu-

Xaa$_{B16}$-Leu-Val-Cys-Gly-Glu-Arg-Gly-Xaa$_{B24}$-Xaa$_{B25}$-

Xaa$_{B26}$-Xaa$_{B27}$-Xaa$_{B28}$-Xaa$_{B29}$-Xaa$_{B30}$-Xaa$_{B31}$-Xaa$_{B32}$ wherein
Xaa$_{A(-2)}$ is absent or Gly;
Xaa$_{A(-1)}$ is absent or Pro;
Xaa$_{A0}$ is absent or Pro;
Xaa$_{A8}$ is independently selected from Thr and His;
Xaa$_{A12}$ is independently selected from Ser, Asp and Glu;
Xaa$_{A13}$ is independently selected from Leu, Thr, Asn, Asp, Gln, His, Lys, Gly, Arg, Pro, Ser and Glu;
Xaa$_{A14}$ is independently selected from Tyr, Thr, Asn, Asp, Gln, His, Lys, Gly, Arg, Pro, Ser and Glu;
Xaa$_{A15}$ is independently selected from Gln, Asp and Glu;
Xaa$_{A18}$ is independently selected from Asn, Lys and Gln;
Xaa$_{A21}$ is independently selected from Asn and Gln;
Xaa$_{A22}$ is absent or Lys;
Xaa$_{B(-2)}$ is absent or Gly;
Xaa$_{B(-1)}$ is absent or Pro;
Xaa$_{B0}$ is absent or Pro;
Xaa$_{B1}$ is absent or independently selected from Phe and Glu;
Xaa$_{B2}$ is absent or Val;
Xaa$_{B3}$ is absent or independently selected from Asn and Gln;
Xaa$_{B4}$ is independently selected from Gln and Glu;
Xaa$_{B10}$ is independently selected from His, Asp, Pro and Glu;
Xaa$_{B16}$ is independently selected from Tyr, Asp, Gln, His, Arg, and Glu;
Xaa$_{B24}$ is independently selected from Phe and His;
Xaa$_{B25}$ is independently selected from Phe and His;
Xaa$_{B26}$ is absent or independently selected from Tyr, His, Thr, Gly and Asp;
Xaa$_{B27}$ is absent or independently selected from Thr, Asn, Asp, Gln, His, Lys, Gly, Arg, Pro, Ser and Glu;
Xaa$_{B28}$ is absent or independently selected from Pro, His, Gly and Asp;
Xaa$_{B29}$ is absent or independently selected from Lys and Gln;
Xaa$_{B30}$ is absent or Thr;
Xaa$_{B31}$ is absent or Leu;
Xaa$_{B32}$ is absent or Glu;
the C-terminal may optionally be derivatized as an amide;
wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge;

wherein optionally the N-terminal A-chain amino acid sequence is connected to the C-terminal B-chain amino acid sequence by an amino acid sequence comprising 3-7 amino acids to form a single chain insulin molecule, wherein optionally the N-terminal of the B-chain is extended with 1-10 amino acids;
wherein if Xaa$_{A8}$ is Thr and Xaa$_{A12}$ is Ser and Xaa$_{A13}$ is Leu and Xaa$_{A14}$ is Tyr then Xaa$_{A15}$ is Glu or Asp; and
wherein if Xaa$_{B24}$ is Phe and Xaa$_{B25}$ is Phe and Xaa$_{B26}$ is Tyr and Xaa$_{B27}$ is Thr and Xaa$_{B28}$ is Pro then Xaa$_{B29}$ Gln.
Embodiment 18. An insulin analogue according to any of the embodiments 1-4 or 12-14 comprising an A-chain amino acid sequence of formula 3:

Formula (3)

(SEQ ID No: 3)
Gly-Ile-Val-Glu-Gln-Cys-Cys-Xaa$_{A8}$-Ser-Ile-Cys-

Xaa$_{A12}$-Xaa$_{A13}$-Xaa$_{A14}$-Xaa$_{A15}$-Leu-Glu-Xaa$_{A18}$-Tyr-

Cys-Xaa$_{A21}$ and a B-chain amino acid sequence of formula 4:

Formula (4)

(SEQ ID No: 4)
Xaa$_{B1}$-Val-Xaa$_{B3}$-Xaa$_{B4}$-His-Leu-Cys-Gly-Ser-Xaa$_{B10}$-

Leu-Val-Glu-Ala-Leu-Xaa$_{B16}$-Leu-Val-Cys-Gly-Glu-

Arg-Gly-Xaa$_{B24}$-His-Xaa$_{B26}$-Xaa$_{B27}$-Xaa$_{B28}$-Xaa$_{B29}$-

Xaa$_{B30}$ wherein
Xaa$_{A8}$ is independently selected from Thr and His;
Xaa$_{A12}$ is independently selected from Ser, Asp and Glu;
Xaa$_{A13}$ is independently selected from Leu, Thr, Asn, Asp, Gln, His, Lys, Gly, Arg, Pro, Ser and Glu;
Xaa$_{A14}$ is independently selected from Thr, Asn, Asp, Gln, His, Lys, Gly, Arg, Pro, Ser and Glu;
Xaa$_{A15}$ is independently selected from Gln, Asp and Glu;
Xaa$_{A18}$ is independently selected from Asn, Lys and Gln;
Xaa$_{A21}$ is independently selected from Asn, and Gln;
Xaa$_{B1}$ is independently selected from Phe and Glu;
Xaa$_{B3}$ is independently selected from Asn and Gln;
Xaa$_{B4}$ is independently selected from Gln and Glu;
Xaa$_{B10}$ is independently selected from His, Asp, Pro and Glu;
Xaa$_{B16}$ is independently selected from Tyr, Asp, Gln, His, Arg, and Glu;
Xaa$_{B24}$ is independently selected from Phe and His;
Xaa$_{B26}$ is absent or independently selected from Tyr, His, Thr, Gly and Asp;
Xaa$_{B27}$ is absent or independently selected from Thr, Asn, Asp, Gln, His, Lys, Gly, Arg, Pro, Ser and Glu;
Xaa$_{B28}$ is absent or independently selected from Pro, His, Gly and Asp;
Xaa$_{B29}$ is absent or independently selected from Lys and Gln;
Xaa$_{B30}$ is absent or Thr;
the C-terminal may optionally be derivatized as an amide;
wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

Embodiment 19. An insulin analogue according to embodiment 18, wherein
Xaa$_{A8}$ is independently selected from Thr and His;
Xaa$_{A12}$ is independently selected from Ser and Glu;
Xaa$_{A13}$ is independently selected from Leu, Thr, Asn, Asp, Gln, His, Lys, Gly, Arg, Pro, Ser and Glu;
Xaa$_{A14}$ is independently selected from Asp, His, and Glu;
Xaa$_{A15}$ is independently selected from Gln and Glu;
Xaa$_{A18}$ is independently selected from Asn, Lys and Gln;
Xaa$_{A21}$ is independently selected from Asn, and Gln;
Xaa$_{B1}$ is independently selected from Phe and Glu;
Xaa$_{B3}$ is independently selected from Asn and Gln;
Xaa$_{B4}$ is independently selected from Gln and Glu;
Xaa$_{B10}$ is independently selected from His, Asp, Pro and Glu;
Xaa$_{B16}$ is independently selected from Tyr, Asp, Gln, His, Arg, and Glu;
Xaa$_{B24}$ is independently selected from Phe and His;
Xaa$_{B26}$ is independently selected from Tyr, Thr, Gly and Asp;
Xaa$_{B27}$ is independently selected from Thr, Asn, Asp, Gln, His, Lys, Gly, Arg, and Glu;
Xaa$_{B28}$ is independently selected from Pro, Gly and Asp;
Xaa$_{B29}$ is independently selected from Lys and Gln;
Xaa$_{B30}$ is absent or Thr;
the C-terminal may optionally be derivatized as an amide;
wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

Embodiment 20. An insulin analogue according to any of the embodiments 1-16 wherein the C-terminal B-chain is connected to the N-terminal A-chain with 3-15 amino acids or 3-7 amino acids, to form a single chain insulin molecule, wherein optionally the N-terminal of the B-chain is extended with 1-10 amino acids.

Embodiment 21. A pharmaceutical composition comprising a biologically active amount of the insulin analogue according to any of the embodiments 1-20 and a pharmaceutically acceptable carrier.

Embodiment 22. A pharmaceutical composition comprising two or more insulin analogues according to any of the embodiments 1-20 wherein each analogue is defined by having at least one mutation, which is absent in at least one of the other variants.

Embodiment 23. A pharmaceutical composition according to any of the embodiments 11-20 which further comprises a pharmaceutical acceptable carrier and/or excipient, and optionally an adjuvant.

Embodiment 24. A method for the treatment of diabetes mellitus in a subject comprising administering to a subject an insulin analogue according to any of the embodiments 1-20 or a pharmaceutical composition according to any of the embodiments 2121-23.

Embodiment 25. A method of reducing the blood glucose level in mammals by administrating to a patient in need of such treatment a therapeutically active dose of an insulin analogue according to any of the embodiments 1-20 or a pharmaceutical composition according to any of the embodiments 2121-23.

Embodiment 26. Method according to embodiment 24 or 25 being an oral administration.

Embodiment 27. Method according to embodiment 24 or 25 being parenteral administration.

Embodiment 28. Method according to embodiment 24 or 25 being intratracheal administration.

Embodiment 29. An insulin analogue according to any of the embodiments 1-20 for use as a pharmaceutical in the treatment or prevention of hyperglycemia, type 2 diabetes, impaired glucose tolerance, type 1 diabetes, obesity, syndrome X and dyslipidemia.

Embodiment 30. An insulin analogue according to any of the embodiments 1-20 for use as a pharmaceutical in delaying or preventing disease progression in type 2 diabetes.

Embodiment 31. An insulin analogue according to any of the embodiments 1-20 for use as a pharmaceutical in decreasing food intake, decreasing β-cell apoptosis, increasing β-cell function and β-cell mass, and/or for restoring glucose sensitivity to β-cells.

Embodiment 32. A nucleic acid sequence encoding an insulin analogue according to any of the embodiments 1-20, a derivative thereof, a partial sequence thereof, a degenerated sequence thereof or a sequence which hybridises thereto under stringent conditions.

Embodiment 33. A nucleic acid sequence encoding a precursor of an insulin analogue according to any of the embodiments 1-20, a derivative thereof, a partial sequence thereof, a degenerated sequence thereof or a sequence which hybridises thereto under stringent conditions.

Embodiment 34. An expression vector comprising a nucleic acid sequence according to embodiment 32 or 33.

Embodiment 35. A host cell comprising an expression vector according to embodiment 34.

Embodiment 36. A method of producing an insulin analogue comprising the step of cultivating the host cell of embodiment 35.

Embodiment 37. A method of preparing an insulin analogue according to any of the embodiments 1-20 wherein the substitution of amino acids is carried out by site-directed mutagenesis.

Embodiment 38. A process for preparing a pharmaceutical composition according to any of the embodiments 21-23 comprising mixing an insulin analogue according to any of the embodiments 1-20 with pharmaceutically acceptable substances and/or excipients.

Embodiment 39. A pharmaceutical composition obtainable by the process according to embodiment 38.

Insulin is a polypeptide hormone secreted by β-cells of the pancreas. Insulin consists of two polypeptide chains, A and B, which are linked by two inter-chain disulphide bridges. Furthermore, the A-chain features one intra-chain disulphide bridge.

The hormone is synthesized as a single-chain precursor proinsulin (preproinsulin) consisting of a prepeptide of 24 amino acid followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

The insulin analogues according to the invention may comprise further mutations. A mutation in an insulin molecule may be in the form of a substitution, a deletion or an addition of an amino acid residue in the A and/or B chain of the naturally occurring insulin molecule.

With "desB30" or "B(1-29)" is meant natural insulin B chain lacking the B30 amino acid residue and "A(1-21)" means the natural insulin A chain. The mini C-peptide and its amino acid sequence are indicated in the three letter amino acid code.

Herein terms like A1, A2, A3 etc. indicates the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively.

Herein the terms A(0) or B(0) indicate the positions N-terminally neighbouring A1 or B1, respectively. The terms A(−1) or B(−1) indicate the positions of the first amino acids N-terminally to A(0) or B(0), respectively. Thus A(−2) and B(−2) indicate positions N-terminally to A(−1) and B(−1), respectively, A(−3) and B(−3) indicate positions N-terminally to A(−2) and B(−2), respectively, and so forth.

The term connecting peptide covers a peptide chain which can connect the C-terminal amino acid residue of the B-chain with the N-terminal amino acid residue of the A-chain in insulin.

The term pro-peptide means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analogue thereof.

The term "diabetes" includes type 1 diabetes, type 2 diabetes and other states that cause hyperglycaemia.

The term "treatment" of a disease includes treatment, prevention or alleviation of the disease.

In one embodiment of the invention the insulin analogue is particularly suitable for oral administration.

Hydrophobic amino acids are herein to be understood as the naturally occurring amino acids tryptophan (Trp, W), phenylalanine (Phe, F), valine (Val, V), isoleucine (Ile, I), leucine (Leu, L) and tyrosine (Tyr, Y) (with the three-letter and the one-letter abbreviation in brackets).

Hydrophilic amino acids are herein to be understood as natural amino acids that are not hydrophobic amino acids according to the definition above. In one embodiment hydrophilic acids according to the invention are selected from the group consisting of: Glutamic acid (Glu, E), aspartic acid (Asp, D), histidine (His, H), glutamine (Gln, Q), asparagine (Asn, N), serine (Ser, S), threonine (Thr, T), proline (Pro, P), glycine (Gly, G), lysine (Lys, K) and arginine (Arg, R). In a further embodiment hydrophilic amino acids according to the invention are selected from the group consisting of: Glutamic acid (Glu, E), aspartic acid (Asp, D), histidine (His, H), glutamine (Gln, Q), asparagine (Asn, N), lysine (Lys, K) and arginine (Arg, R).

"An insulin" according to the invention is herein to be understood as human insulin, an insulin analogue or an insulin derivative.

The term "parent insulin" as used herein is intended to mean an insulin before any mutations according to the invention have been applied thereto. Non-limiting examples of parent insulins are e.g. a wild-type insulin such as human insulin or porcine insulin, an analogue of human insulin or a derivative of human insulin or an insulin analogue such as human insulin or an insulin analogue which has been PEGylated or acylated.

In one embodiment a parent insulin according to the invention is selected from the group consisting of:
Human Insulin,
an insulin analogue of human insulin wherein the amino acid residue in position B28 of is Pro, Asp, Lys, Leu, Val, or Ala and the amino acid residue in position B29 is Lys or Pro and optionally the amino acid residue in position B30 is deleted,
an insulin analogue which is des(B28-B30) human insulin, des(B27) human insulin or des(B30) human insulin,
an insulin analogue of human insulin wherein the amino acid residue in position B3 is Lys and the amino acid residue in position B29 is Glu or Asp,
an insulin analogue of human insulin wherein the amino acid residue in position A21 is Gly and wherein the insulin analogue is further extended in the C-terminal with two arginine residues,
an insulin derivative wherein the amino acid residue in position B30 is substituted with a threonine methyl ester, and
an insulin derivative wherein to the NE position of lysine in the position B29 of des(B30) human insulin a tetradecanoyl chain is attached.

In one embodiment a parent insulin according to the invention is selected from the group consisting of:
Human Insulin;
DesB30 human insulin;
AspB28 human insulin;
AspB28,DesB30 human insulin;
LysB3, GluB29 human insulin;
LysB28, ProB29 human insulin;
GlyA21, ArgB31, ArgB32 human insulin; and
DesB30, ArgB31, ArgB32 human insulin.

The term "insulin analogue" as used herein means a modified insulin wherein one or more amino acid residues of the insulin have been substituted by other amino acid residues and/or wherein one or more amino acid residues have been deleted from the insulin and/or wherein one or more amino acid residues have been added to the insulin.

In one embodiment an insulin analogue comprises less than 8 modifications (substitutions, deletions, additions) relative to the parent insulin. In one embodiment an insulin analogue comprises less than 7 modifications (substitutions, deletions, additions) relative to the parent insulin. In one embodiment an insulin analogue comprises less than 6 modifications (substitutions, deletions, additions) relative to the parent insulin. In another embodiment an insulin analogue comprises less than 5 modifications (substitutions, deletions, additions) relative to the parent insulin. In another embodiment an insulin analogue comprises less than 4 modifications (substitutions, deletions, additions) relative to the parent insulin. In another embodiment an insulin analogue comprises less than 3 modifications (substitutions, deletions, additions) relative to the parent insulin. In another embodiment an insulin analogue comprises less than 2 modifications (substitutions, deletions, additions) relative to the parent insulin.

The term "insulin derivative" as used herein means a chemically modified parent insulin or an analogue thereof, wherein at least one substituent is not present in the parent protein or an analogue thereof, i.e. a parent protein which has been covalently modified. Typical modifications are amides, carbohydrates, alkyl groups, acyl groups, esters, PEGylations and the like. Examples of derivatives of human insulin according to the invention are threonine methyl ester-B30 human insulin, Nε-B29-tetradecanoyl des(B30) human insulin, Nε-B29-tetradecanoyl GlnB3 des(B30) human insulin), Nε-B29-tridecanoyl human insulin, Nε-B29-tetradecanoyl human insulin, Nε-B29-decanoyl human insulin and Nε-B29-dodecanoyl human insulin.

The term "human insulin" as used herein means the human hormone whose structure and properties are well-known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

Mutations in the insulin molecule is denoted stating the chain (A or B), the position, and the three letter code for the amino acid substituting the native amino acid. By "desB30" is meant a natural insulin B chain or an analogue thereof lacking the B30 amino acid. Thus, A21Gly, B28Asp, desB30 human insulin is an analogue of human insulin where position 21 in the A chain is mutated to glycine, position 28 in the B chain is mutated to aspartic acid, and position 30 in the B chain is deleted.

A "protease" or a "protease enzyme" is a digestive enzyme which degrades proteins and peptides and which is found in various tissues of the human body such as e.g. the stomach (pepsin), the intestinal lumen (chymotrypsin, trypsin, elastase, carboxypeptidases, etc.) or mucosal surfaces of the GI tract (aminopeptidases, carboxypeptidases, enteropeptidases, dipeptidyl peptidases, endopeptidases, etc.), the liver (Insulin degrading enzyme, cathepsin D etc), and in other tissues.

A proteolytically stable insulin analogue is herein to be understood as an insulin analogue, which is subjected to slower degradation by one or more proteases relative to human insulin. In one embodiment a proteolytically stable insulin analogue according to the invention is subjected to slower degradation by one or more proteases relative to the parent insulin. In a further embodiment of the invention an insulin analogue according to the invention is stabilized against degradation by one or more enzymes selected from the group consisting of: pepsin (such as e.g. the isoforms pepsin A, pepsin B, pepsin C and/or pepsin F), chymotrypsin (such as e.g. the isoforms chymotrypsin A, chymotrypsin B and/or chymotrypsin C), trypsin, Insulin-Degrading Enzyme (IDE), elastase (such as e.g. the isoforms pancreatic elastase I and/or II), carboxypeptidase (e.g. the isoforms carboxypeptidase A, carboxypeptidase A2 and/or carboxypeptidase B), aminopeptidase, cathepsin D and other enzymes present in intestinal extracts derived from rat, pig or human.

In one embodiment an insulin analogue according to the invention is stabilized against degradation by one or more enzymes selected from the group consisting of: chymotrypsin, trypsin, Insulin-Degrading Enzyme (IDE), elastase, carboxypeptidases, aminopeptidases and cathepsin D. In a further embodiment an insulin analogue according to the invention is stabilized against degradation by one or more enzymes selected from the group consisting of: chymotrypsin, carboxypeptidases and IDE. In a yet further embodiment an insulin analogue according to the invention is stabilized against degradation by one or more enzymes selected from: chymotrypsin and carboxypeptidases.

T½ may be determined as described in the Examples as a measure of the proteolytical stability of an insulin analogue according to the invention towards protease enzymes such as chymotrypsin, pepsin and/or carboxypeptidase A. In one embodiment of the invention T½ is increased relative to human insulin. In a further embodiment T½ is increased relative to the parent insulin. In a yet further embodiment T½ is increased at least 2-fold relative to the parent insulin. In a yet further embodiment T½ is increased at least 3-fold relative to the parent insulin. In a yet further embodiment T½ is increased at least 4-fold relative to the parent insulin. In a yet further embodiment T½ is increased at least 5-fold relative to the parent insulin. In a yet further embodiment T½ is increased at least 10-fold relative to the parent insulin.

Protease cleavage sites (herein also mentioned as protease sites) are to be understood as amino acid residues that are recognized by proteases and/or amino acid residues whose peptide bond is cleaved by proteases. Protease cleavage sites may be determined by determining cleavage "hot-spots" by HPLC, MS or LC-MS analyses and/or by prediction based on enzyme specificity of the protease enzyme for which the protease cleavage site is to be determined. A skilled person in the art will know how to determine protease cleavage sites for example based on enzyme specificities as for example described in Handbook of Proteolytical Enzymes, 2nd ed., Barrett, A. J., Rawlings, N. D., Woesner, J. F. editors, Elsevier Academic Press 2004. For example chymotrypsin is predicted to cleave peptide bonds C-terminal to aromatic residues (Trp, Tyr, Phe or Leu), that are not followed by Pro. Similarly, trypsin is predicted to cleave peptide bonds C-terminal to basic residues Lys or Arg, that are not followed by Pro, elastase is predicted to cleave residues C-terminal to Ala, Val, Gly or Ser and carboxypeptidase A will remove any C-terminal amino acid, but not Arg, Lys or Pro. Insulin-degrading enzyme (IDE) is predicted to cleave the following positions of human insulin B9-10, B10-11, B13-14, B14-15, B24-25, B25-26, A13-14 and A14-15.

The term substituting (an) amino acid "within or in close proximity" to a protease cleavage site is herein used to indicate the substitution of an amino acid within or in close proximity to a position of the parent insulin which has been determined to be a protease cleavage site. In one embodiment two or more hydrophobic amino acids within or in close proximity to two or more protease sites on an insulin are substituted, wherein said hydrophobic amino acids are substituted with hydrophilic amino acids. In a further embodiment two or more hydrophobic amino acids within two or more protease sites on an insulin are substituted with hydrophilic amino acids. In a yet further embodiment two or more hydrophobic amino acids situated next to two or more protease sites on an insulin are substituted with hydrophilic amino acids. In a still further embodiment two or more hydrophobic amino acids situated two amino acids away from to two or more protease sites on an insulin are substituted with hydrophilic amino acids. In a yet further embodiment two or more hydrophobic amino acids situated three amino acids away from two or more protease sites on an insulin are substituted with hydrophilic amino acids. In a still further embodiment two or more hydrophobic amino acids situated up to four amino acids away from two or more protease sites on an insulin are substituted with hydrophilic amino acids. In a yet further embodiment two or more hydrophobic amino acids situated one, two or three amino acids away from or within two or more protease sites on an insulin are substituted with hydrophilic amino acids. In a still further embodiment two or more hydrophobic amino acids situated one or two amino acids away from or within two or more protease sites on an insulin are substituted with hydrophilic amino acids. In a yet further embodiment two or more hydrophobic amino acids situated next to or within two or more protease sites on an insulin are substituted with hydrophilic amino acids.

An insulin analogue according to the invention may have a net charge which is different than the net charge of the parent insulin. In one embodiment the net charge of an insulin analogue according to the invention is more positive than the net charge of the parent insulin. In one embodiment the net charge of an insulin analogue according to the invention is more negative than the net charge of the parent insulin. In one embodiment the average positive net charge of an insulin analogue according to the invention is between 0.5 and 5 as measured in an aqueous solution. In one embodiment the average positive net charge of an insulin analogue according to the invention is between 1 and 5. In one embodiment the average positive net charge of an insulin analogue according to the invention is between 1 and 4. In one embodiment the average positive net charge of an insulin analogue according to the invention is between 1 and 3. In one embodiment the average positive net charge of an insulin analogue according to the invention is between 2 and 3. In one embodiment the average negative net charge of an insulin analogue according to the invention is between −0.5 and −5 as measured in an aqueous solution. In one embodiment the average negative net charge of an insulin analogue according to the invention is between −1 and −5. In one embodiment the average negative net charge of an insulin analogue according to the invention is between −1 and −4. In one embodiment the average negative net charge of an insulin analogue according to the invention is between −1 and −3. In one embodiment the average negative net charge of an insulin analogue according to the invention is between −2 and −3.

In one embodiment an insulin analogue according to the invention may have increased solubility relative to human insulin. In a further embodiment an insulin analogue according to the invention has increased solubility relative to human insulin at pH 3-9. In a yet further embodiment an insulin analogue according to the invention has increased solubility relative to human insulin at pH 4-8.5. In a still further embodiment an insulin analogue according to the invention has increased solubility relative to human insulin at pH 4-8. In a yet further embodiment an insulin analogue according to the invention has increased solubility relative to human insulin at pH 4.5-8. In a further embodiment an insulin analogue according to the invention has increased solubility relative to human insulin at pH 5-8. In a yet further embodiment an insulin analogue according to the invention has increased solubility relative to human insulin at pH 5.5-8. In a further embodiment an insulin analogue according to the invention has increased solubility relative to human insulin at pH 6-8.

In one embodiment an insulin analogue according to the invention has increased solubility relative to human insulin at pH 2-4.

In one embodiment an insulin analogue according to the invention may have increased solubility relative to the parent insulin. In a further embodiment an insulin analogue according to the invention has increased solubility relative to the parent insulin at pH 3-9. In a yet further embodiment an insulin analogue according to the invention has increased solubility relative to parent insulin at pH 4-8.5. In a still further embodiment an insulin analogue according to the invention has increased solubility relative to parent insulin at pH 4-8. In a yet further embodiment an insulin analogue according to the invention has increased solubility relative to parent insulin at pH 4.5-8. In a still further embodiment an insulin analogue according to the invention has increased solubility relative to parent insulin at pH 5-8. In a yet further embodiment an insulin analogue according to the invention has increased solubility relative to parent insulin at pH 5.5-8. In a further embodiment an insulin analogue according to the invention has increased solubility relative to parent insulin at pH 6-8.

In one embodiment an insulin analogue according to the invention has increased solubility relative to parent insulin at pH 2-4.

By "increased solubility at a given pH" is meant that a larger concentration of an insulin analogue of the invention dissolves in an aqueous or buffer solution at the pH of the solution relative to the insulin it is compared to, i.e. human insulin or the parent insulin. Methods for determining whether the insulin contained in a solution is dissolved are known in the art.

In one embodiment, the solution may be subjected to centrifugation for 20 minutes at 30,000 g and then the insulin concentration in the supernatant may be determined by RP-HPLC. If this concentration is equal within experimental error to the insulin concentration originally used to make the composition, then the insulin is fully soluble in the composition of the invention.

In another embodiment, the solubility of the insulin in a composition of the invention can simply be determined by examining by eye the container in which the composition is contained. The insulin is soluble if the solution is clear to the eye and no particulate matter is either suspended or precipitated on the sides/bottom of the container.

An insulin analogue according to the invention may have increased potency and/or bioavalability relative to the parent insulin when compared upon measurement.

Standard assays for measuring insulin potency or bioavailability are known to the person skilled in the art and include inter alia (1) insulin radioreceptorassays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction; (2) lipogenesis assays, performed e.g. with rat adipocytes, in which relative insulin potency is defined as the ratio of insulin to insulin analogue required to achieve 50% of the maximum conversion of [3-$^3$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radio-immunoassays which can determine the immunogenicity of insulin analogues by measuring the effectiveness by which insulin or an insulin analogue competes with $^{125}$I-insulin in binding to specific anti-insulin antibodies; and (5) other assays which measure the binding of insulin or an insulin analogue to antibodies in animal blood plasma samples, such as ELISA assays possessing specific insulin antibodies.

Insulin analogues according to the invention may optionally be analyzed for further protease sites which may be subject to further substitutions of one or more hydrophobic amino acids with hydrophilic amino acids. An insulin analogue according to the invention may be an insulin analogue which has at least two hydrophilic acids in protease sites compared to the parent insulin, the first modified insulin, and which has further at least one amino acid substitution in a new protease site of the first modified insulin wherein at least one hydrophobic amino acid has been substituted with at least one hydrophilic amino acid.

In one embodiment an insulin analogue is provided wherein the C terminal B chain is connected to the N terminal A chain with 3-15 amino acids. Such an insulin analogue is herein denoted "single-chain insulin" or "SCI" and has the general structure B-C-A wherein B is the human B insulin chain or an analogue or derivative thereof, A is the human insulin A chain or an analogue or derivative and C is the connecting peptide chain of 3-15 amino acid residues normally connecting B30 with A1. If the B chain is a desB30 chain the connecting peptide will connect B29 with A1. The single-chain insulin will contain correctly positioned disulphide bridges (three) as in human insulin that is between CysA7 and CysB7 and between CysA20 and CysB19 and an internal disulfide bridge between CysA6 and CysA11. In one embodiment an insulin analogue is provided wherein the C terminal B chain is connected to the N terminal A chain with 3-7 amino acids.

The present invention is also related to nucleic acid sequences which code for the claimed insulin analogues. In a further embodiment the present invention is related to vectors containing such nucleic acid sequences and host cells containing such nucleic acid sequences or vectors.

In still a further embodiment, the invention relates to a process for producing an insulin analogue comprising (i) culturing a host cell comprising a nucleic acid sequence encoding an insulin precursor; (ii) isolating the insulin precursor from the culture medium and (iii) converting the insulin precursor into an insulin analogue of the invention by in vitro enzymatic conversion.

In still a further embodiment, the invention relates to a process for producing an insulin analogue comprising (i) culturing a host cell comprising a nucleic acid sequence encoding an insulin precursor; (ii) isolating the insulin precursor from the culture medium and (iii) converting the insulin precursor into an insulin analogue of the invention.

In one embodiment of the present invention the host cell is a yeast host cell and in a further embodiment the yeast host cell is selected from the genus *Saccharomyces*. In a further embodiment the yeast host cell is selected from the species *Saccharomyces cerevisiae.*

By "insulin analogue" as used herein is meant a polypeptide derived from the primary structure of a naturally occurring insulin, for example that of human insulin, by deleting and/or substituting at least one amino acid residue occurring in the naturally occuring insulin and/or by adding at least one amino acid residue. The added and/or substituted amino acid residues can either be codable amino acid residues or other naturally occurring amino acid residues.

The insulin analogues according to the present invention may be human insulin or an analogue thereof mutated in one or more positions. In one embodiment the insulin analogues are designed for enhanced stability towards proteases based on the identified protease cleavage sites.

In one embodiment at least one cleavage site subjected to mutation is in a position selected from the group consisting of: B2-3, B6-7, B9-10, B10-11, B13-14, B14-15, B16-17, B22-23, B24-25, B25-26, A13-14, A14-15 and A19-20 of human insulin.

In one embodiment at least one cleavage site subjected to mutation is in a position selected from the group consisting of: B2-3, B6-7, B16-17, B22-23, B24-25 and/or A19-20 of human insulin.

In one embodiment at least one cleavage site subjected to mutation is in position B22-23.

In one embodiment at least one cleavage site subjected to mutation is in a position selected from the group consisting of: B9-10, B10-11, B13-14, B14-15, B24-25, B25-26, A13-14, A14-15.

In one embodiment cleavage sites subjected to mutation are in two or more positions selected from the group consisting of: B2-3, B6-7, B9-10, B10-11, B13-14, B14-15, B16-17, B22-23, B24-25, B25-26, A13-14, A14-15 and A19-20 of human insulin.

In one embodiment cleavage sites subjected to mutation are in two or more positions selected from the group consisting of: B2-3, B6-7, B16-17, B22-23, B24-25 and/or A19-20 of human insulin.

In one embodiment cleavage sites subjected to mutation are in two or more positions selected from the group consisting of: B9-10, B10-11, B13-14, B14-15, B24-25, B25-26, A13-14, A14-15.

In one embodiment an insulin analogue according to the invention is obtained wherein the A-chain of the insulin analogue comprises at least one mutation and the B-chain of the insulin analogue comprises at least one mutation relative to the parent insulin, wherein the at least one mutation in the A-chain is in one or more cleavage sites selected from the group consisting of: A13-14, A14-15 and A19-20 and the at least one mutation in the B-chain is in one or more cleavage sites selected from the group consisting of: B2-3, B6-7, B9-10, B10-11, B13-14, B14-15, B16-17, B22-23, B24-25 and B25-26.

In one embodiment an insulin analogue according to the invention is obtained wherein the A-chain of the insulin analogue comprises one mutation and the B-chain of the insulin analogue comprises at least one mutation relative to the parent insulin, wherein the one mutation in the A-chain is in the cleavage site A19-20 and the at least one mutation in the B-chain is in one or more cleavage sites selected from the group consisting of: B2-3, B6-7, B16-17, B22-23 and B24-25.

In one embodiment an insulin analogue according to the invention is obtained wherein the A-chain of the insulin analogue comprises at least one mutation and the B-chain of the insulin analogue comprises at least one mutation relative to the parent insulin, wherein the at least one mutation in the A-chain is in one or more cleavage sites selected from the group consisting of: A13-14 and A14-15 and the at least one mutation in the B-chain is in one or more cleavage sites selected from the group consisting of: B9-10, B10-11, B13-14, B14-15, B24-25 and B25-26.

Amino acid residues suitable for substitution are selected with the purpose of removing the cleavage sites. In one embodiment amino acids are selected with the additional purpose of increasing the solubility. In a further embodiment the increased solubility is in the pH range 3-9. In a yet further embodiment the increased solubility is in the pH range 4-8. The insulin or insulin analogue may be substituted in one or more positions by any natural amino acid or any natural amino acid may be added to the parent insulin or parent insulin analogue. For the sake of convenience, here follows the names of codable, natural amino acids with the usual three letter codes & one letter codes in parenthesis: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the insulins of this invention are, preferably, amino acids which can be coded for by a nucleic acid. In one embodiment insulin or an insulin analogue is substituted by Gly, Glu, Asp, His, Gln, Asn, Ser, Thr, Lys, Arg and/or Pro and/or Gly, Glu, Asp, His, Gln, Asn, Ser, Thr, Lys, Arg and/or Pro is added to insulin or an insulin analogue. In one embodiment insulin or an insulin analogue is substituted by Glu, Asp, His, Gln, Asn, Lys and/or Arg and/or Glu, Asp, His, Gln, Asn, Lys and/or Arg is added to insulin or an insulin analogue.

The insulin analogues may be such wherein position 25 of the B chain may be modified from the natural Phe residue to His in combination with substitution of the natural Tyr at position A14 to Glu, Asp or His. One or more additional mutations may include desB30 and the insulin analogues could be further modified by N-terminal extension or C-terminal extension of the A-chain and/or the B-chain such as e.g. extension of the N-terminal of the A- and/or B-chain of the insulin analogue with GGP, GGPP, GP or GPP. Further examples include but are not limited to additional mutations wherein one or two Pro residues may be added to positions A0 and/or B0, Leu may be added to position B31 and/or Glu may be added to position B32. One or more additional mutations may be selected from position A8 modified to His, position A21 to Gly, position B1 to Glu or Gln, position B16 to Glu, position B26 to Asp, position B27 to Glu and/or position B28 to Asp.

In one embodiment an insulin analogue according to the invention is selected from the group consisting of:

A14E, B25H, desB30 human insulin;
A14H, B25H, desB30 human insulin;
A14E, B1E, B25H, desB30 human insulin;
A14E, B16E, B25H, desB30 human insulin;
A14E, B25H, B28D, desB30 human insulin;
A14E, B25H, B27E, desB30 human insulin;
A14E, B1E, B25H, B27E, desB30 human insulin;
A14E, B1E, B16E, B25H, B27E, desB30 human insulin;
A8H, A14E, B25H, desB30 human insulin;
A8H, A14E, B25H, B27E, desB30 human insulin;
A8H, A14E, B1E, B25H, desB30 human insulin;
A8H, A14E, B1E, B25H, B27E, desB30 human insulin;
A8H, A14E, B1E, B16E, B25H, B27E, desB30 human insulin;
A8H, A14E, B16E, B25H, desB30 human insulin;
A14E, B25H, B26D, desB30 human insulin;
A14E, B1E, B27E, desB30 human insulin;
A14E, B27E, desB30 human insulin;
A14E, B28D, desB30 human insulin;
A14D, B25H, desB30 human insulin;
A(−1)P, A(0)P, A14E, B25H, desB30 human insulin;
A14E, B(−1)P, B(0)P, B25H, desB30 human insulin;
A(−1)P, A(0)P, A14E, B(−1)P, B(0)P, B25H, desB30 human insulin;
A14E, B25H, B30T, B31L, B32E human insulin;
A14E, B25H human insulin;
A14E, B16H, B25H, desB30 human insulin;
A14E, B10P, B25H, desB30 human insulin;
A14E, B10E, B25H, desB30 human insulin;
A14E, B4E, B25H, desB30 human insulin;
A14H, B16H, B25H, desB30 human insulin;
A14H, B10E, B25H, desB30 human insulin;
A14E, B25H, desB27, desB28, desB29, desB30 human insulin;
A13H, A14E, B10E, B25H, desB30 human insulin;
A13H, A14E, B25H, desB30 human insulin;
A14E, A18Q, B3Q, B25H, desB30 human insulin;
A14E, B24H, B25H, desB30 human insulin;
A8H, A14E, B10D, B25H, B26G, desB27, desB28, desB29, desB30 human insulin;
A8H, A14E, B10D, B25H-amide, desB26, desB27, desB28, desB29, desB30 human insulin;
A14E, B25H, desB26, desB27, desB28, desB29, desB30 human insulin;
A14E, B25H, B26G, desB27, desB28, desB29, desB30 human insulin;
A14E, B25H-amide, desB27, desB28, desB29, desB30 human insulin
A14E, B25H, B26G, B27G, B28G, desB30 human insulin;
A14E, B26G, desB27, desB28, desB29, desB30 human insulin;
A14E, B25H, desB26, desB27, desB28, desB29, desB30 human insulin;
A14E, A18Q, A21Q, B3Q, B25H, desB30 human insulin;
A14E, A18Q, A21Q, B3Q, B25H, B27E, desB30 human insulin;
A14E, A18Q, B3Q, B25H, desB30 human insulin;
A13H, A14E, B1E, B25H, desB30 human insulin;
A13N, A14E, B25H, desB30 human insulin;
A13N, A14E, B1E, B25H, desB30 human insulin;
A(−2)G, A(−1)P, A(0)P, A14E, B25H, desB30 human insulin;
A14E, B(−2)G, B(−1)P, B(0)P, B25H, desB30 human insulin;
A(−2)G, A(−1)P, A(0)P, A14E, B(−2)G, B(−1)P, B(0)P, B25H, desB30 human insulin;
A14E, B27R, B28D, B29K, desB30 human insulin;
A14E, B25H, B27R, B28D, B29K, desB30 human insulin;
A14E, B25H, B26T, B27R, B28D, B29K, desB30 human insulin;
A14E, A18K, B25H, desB27, desB28, desB29, desB30 human insulin;
A14E, A22K, B25H, desB27, desB28, desB29, desB30 human insulin;
A14E, A22K, B25H, desB30 human insulin;
A14E, desB1, desB2, desB3, B25H-amide, desB26, desB27, desB28, desB29, desB30 human insulin;
A14E, desB1, desB2, desB3, B25H, desB27, desB28, desB29, desB30 human insulin;
A14E, desB1, desB2, desB3, B16H, B25H, desB27, desB28, desB29, desB30 human insulin;
A14E, B25H, B27R, desB30 human insulin;
A14E, B25H, B27H, desB30 human insulin;
A14E, B25H, B27R, desB28-B30 human insulin;
A14E, B25H, B27H, desB28-B30 human insulin;
A14E, B25H, B27E, desB28-B30 human insulin;
A14E, B25H, B27K, desB28-B30 human insulin;
A14E, B27K, desB28-B30 human insulin;
A14E, A18Q, B3Q, B25H, desB30 human insulin;
A13E, A14E, B25H, desB30 human insulin;
A12E, A14E, B25H, desB30 human insulin;
A15E, A14E, B25H, desB30 human insulin;
A13E, B25H, desB30 human insulin;
A12E, B25H, desB30 human insulin;
A15E, B25H, desB30 human insulin;
A14E, B25H, desB27, desB30 human insulin;
A14E, B25H, B26D, B27E, desB30 human insulin;
EEAEAEAPK (SEQ ID NO: 5)-B(1-29)-B25H-AAK-A(1-21)-A14E human insulin;
EEAEPK (SEQ ID NO: 6)-B(1-29)-B25H-DGK-A(1-21)-A14E human insulin;
B(1-29)-B25H-AAK-A(1-21)-A14E human insulin;
B(1-29)-B1E, B25H-AAK-A(1-21)-A14E human insulin;
B(1-29)-B25H, B27E-AAK-A(1-21)-A8H, A14E human insulin;
B(1-29)-B1 E, B25H, B27E-AAK-A(1-21).A8H, A14E human insulin;
EEAEAEAPK (SEQ ID NO: 5)-B(1-29)-B16E, B25H-AAK-A(1-21)-A8H. A14E human insulin;
B(1-29)-B25H, B29Q-TGLGGGQ (SEQ ID NO: 7)-A(1-21)-A14E human insulin B(1-29)-B16E, B25H, B29Q-TGLGGGQ (SEQ ID NO: 7)-A(1-21)-A14E human insulin B(1-29)-B25H, B29Q-TGLGGGQ (SEQ ID NO: 7)-A(1-21)-A8H, A14E human insulin A14E, B25H, B27R, desB30 human insulin;
A14E, B25H, B27N, desB30 human insulin;
A14E, B25H, B27D, desB30 human insulin;
A14E, B25H, B27Q, desB30 human insulin;
A14E, B25H, B27E, desB30 human insulin;
A14E, B25H, B27G, desB30 human insulin;
A14E, B25H, B27H, desB30 human insulin;
A14E, B25H, B27K, desB30 human insulin;
A14E, B25H, B27P, desB30 human insulin;
A14E, B25H, B27S, desB30 human insulin;
A14E, B25H, B27T, desB30 human insulin;
A13R, A14E, B25H, desB30 human insulin;
A13N, A14E, B25H, desB30 human insulin;
A13D, A14E, B25H, desB30 human insulin;
A13Q, A14E, B25H, desB30 human insulin;
A13E, A14E, B25H, desB30 human insulin;
A13G, A14E, B25H, desB30 human insulin;
A13H, A14E, B25H, desB30 human insulin;
A13K, A14E, B25H, desB30 human insulin;
A13P, A14E, B25H, desB30 human insulin;
A13S, A14E, B25H, desB30 human insulin;
A13T, A14E, B25H, desB30 human insulin;
A14E, B16R, B25H, desB30 human insulin;
A14E, B16D, B25H, desB30 human insulin;
A14E, B16Q, B25H, desB30 human insulin;
A14E, B16E, B25H, desB30 human insulin;
A14E, B16H, B25H, desB30 human insulin;
A14R, B25H, desB30 human insulin;
A14N, B25H, desB30 human insulin;
A14D, B25H, desB30 human insulin;
A14Q, B25H, desB30 human insulin;
A14E, B25H, desB30 human insulin;
A14G, B25H, desB30 human insulin;
A14H, B25H, desB30 human insulin;
A8H, B10D, B25H human insulin; and
A8H, A14E, B10E, B25H, desB30 human insulin.

Insulin is a polypeptide hormone secreted by β-cells of the pancreas and consists of two polypeptide chains, A and B, which are linked by two inter-chain disulphide bridges. Furthermore, the A-chain features one intra-chain disulphide bridge.

The hormone is synthesized as a single-chain precursor proinsulin (preproinsulin) consisting of a prepeptide of 24 amino acid followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

Three major methods have been used for the production of human insulin in microorganisms. Two involve *Escherichia coli*, with either the expression of a large fusion protein in the cytoplasm (Frank et al. (1981) in Peptides: Proceedings of the 7$^{th}$ American Peptide Chemistry Symposium (Rich & Gross, eds.), Pierce Chemical Co., Rockford, Ill. pp 729-739), or use of a signal peptide to enable secretion into the periplasmic space (Chan et al. (1981) PNAS 78:5401-5404). A third method utilizes *Saccharomyces cerevisiae* to secrete an insulin precursor into the medium (Thim et al. (1986) PNAS 83:6766-6770). The prior art discloses a number of insulin precursors which are expressed in either *E. coli* or *Saccharomyces cerevisiae*, vide U.S. Pat. No. 5,962,267, WO 95/16708, EP 0055945, EP 0163529, EP 0347845 and EP 0741188.

The insulin analogues are produced by expressing a DNA sequence encoding the insulin analogue in question in a suitable host cell by well known technique as disclosed in e.g. U.S. Pat. No. 6,500,645. The insulin analogue is either expressed directly or as a precursor molecule which has an N-terminal extension on the B-chain. This N-terminal extension may have the function of increasing the yield of the directly expressed product and may be of up to 15 amino acid residues long. The N-terminal extension is to be cleaved of in vitro after isolation from the culture broth and will therefore have a cleavage site next to B1. N-terminal extensions of the type suitable in the present invention are disclosed in U.S. Pat. No. 5,395,922, and European Patent No. 765,395A.

The isolated insulin analogue can be acylated in the desired position by well know acylation methods and examples of such insulin analogues are described e.g. in the European patent applications having the publication Nos. EP 214826, EP 375437 and EP 383472.

The nucleic acid sequence coding for the respective insulin analogue polypeptide may be prepared synthetically by established standard methods, e.g. the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The nucleic acid sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant vector capable of replicating in the selected microorganism or host cell and which carries a nucleic acid sequence encoding the insulin analogue polypeptide in question may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In one embodiment, the recombinant expression vector is capable of replicating in yeast. Examples of sequences which enable the vector to replicate in yeast are the yeast plasmid 2 µm replication genes REP 1-3 and origin of replication.

The vectors may contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40:125-130).

In the vector, the nucleic acid sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The nucleic acid construct will also typically be operably connected to a suitable terminator. In yeast a suitable terminator is the TPI terminator (Alber et al. (1982) J. Mol. Appl. Genet. 1:419-434).

The procedures used to ligate the individual nucleic acid sequences contained in the expression vector such as DNA coding for the desired insulin analogue polypeptide, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin analogue polypeptides of the invention, and subsequently inserting this fragment into a suitable expression vector, or by sequentially inserting DNA fragments containing genetic information for the individual elements (such as the signal, pro-peptide, connecting peptide, A and B chains) followed by ligation.

The vector comprising such nucleic acid sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In a preferred embodiment, the host cell is a yeast cell. The yeast organism used in the process of the invention may be any suitable yeast organism which, on cultivation, produces large amounts of the single chain insulin of the invention. Examples of suitable yeast organisms are strains selected from the yeast species *Saccharomyces cerevisiae*, *Saccharomyces kluyveri*, *Schizosaccharomyces pombe*, *Sacchoromyces uvarum*, *Kluyveromyces lactis*, *Hansenula polymorpha*, *Pichia pastoris*, *Pichia methanolica*, *Pichia kluyveri*, *Yarrowia lipolytica*, *Candida* sp., *Candida utilis*, *Candida cacaoi*, *Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted insulin analogue polypeptide, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

Pharmaceutical Compositions

Another object of the present invention is to provide a pharmaceutical formulation comprising an insulin analogue according to the present invention which is present in a concentration from 0.1 mg/ml to 500 mg/ml, and wherein said formulation has a pH from 2.0 to 10.0. The formulation may further comprise protease inhibitor(s), a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further embodiment the invention relates to a pharmaceutical formulation comprising an aqueous solution of an insulin analogue of the present invention, and a buffer, wherein said insulin analogue is present in a concentration from 0.1 mg/ml or above, and wherein said formulation has a pH from about 2.0 to about 10.0.

Formulations intended for oral use may be prepared according to any known method, and such formulations may contain one or more agents selected from the group consisting of sweetening agents, flavouring agents, colouring agents, and preserving agents in order to provide pharmaceutically elegant and palatable preparations. Tablets may contain the active ingredient in a mixture with non-toxic pharmaceutically-acceptable excipients which are suitable for the manufacture of tablets. These excipients may be for example, inert diluents, such as mannitol, maltodextrin, kaolin, calcium carbonate, sodium carbonate, lactose, calcium phosphate or sodium phosphate; granulating and disintegrating agents, for example corn starch; binding agents, for example, starch, gelatine, polymers or acacia; and lubricating agents, for example magnesium stearate, stearic acid or talc. The tablets may be uncoated or they may be coated by known techniques to delay disintegration or release of the therapeutically active polypeptide.

The orally administerable formulations of the present invention may be prepared and administered according to methods well known in pharmaceutical chemistry, see Remington's Pharmaceutical Sciences, $17^{th}$ ed. (A. Osol ed., 1985).

In one embodiment of the invention, the pharmaceutical compositions of the present invention may be administered by means of solid dosage forms such as tablets and capsules. The tablets may be prepared by wet granulation, by dry granulation, by direct compression or melt granulation.

Tablets for this invention may be prepared utilizing conventional tabletting techniques. A general method of manufacture involves blending of an insulin analogue, a water-soluble diluent, hydrophilic binder and optionally a portion of a disintegrant. This blend is then granulated with an aqueous solution of the hydrophilic binder or an aqueous solution of the hydrophilic binder and surfactant and milled, if necessary. The granules are dried and reduced to a suitable size. Any other ingredients, such as lubricants, (e.g. magnesium stearate) and additional disintegrants, are added to the granules and mixed. This mixture is then compressed into a suitable size and shape using conventional tabletting machines such as a rotary tablet press. The tablets may be film coated by techniques well known in the art.

Formulations for oral use may also be presented as hard or soft gelatine capsules where the active ingredient is mixed with an inert solid diluent, for example, such as mannitol, maltodextrin, calcium carbonate, sodium carbonate, lactose, kaolin, calcium phosphate or sodium phosphate, or a soft gelatine capsule wherein the active ingredient is mixed with water or an oil medium, for example peanut oil, liquid paraffin, or olive oil.

Capsules for this invention may be prepared utilizing conventional methods. A general method of manufacture involves blending a therapeutically active peptide, alginate, a water-soluble diluent, a hydrophilic binder, and optionally a portion of a disintegrant. This blend is then granulated with an aqueous solution of the hydrophilic binder or an aqueous solution of the hydrophilic binder and surfactant in water, and milled, if necessary. The granules are dried and reduced to a suitable size. Any other ingredients, such as a lubricant, are added to the granules and mixed. The resulting mixture is then filled into a suitable size hard-shell gelatin capsule using conventional capsule-filling machines.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. The preservative is present in an amount sufficient to obtain a preserving effect. The amount of preservative in a pharmaceutical formulation is the well-known to the skilled person and may be determined from e.g. literature in the field and/or the known amount(s) of preservative in e.g. commercial products. Each one of these specific preservatives constitutes an alternative embodiment of the invention. The use of a preservative in pharmaceutical compositions is well-known to the skilled person. For convenience reference is made to Remington: *The Science and Practice of Pharmacy*, $19^{th}$ edition, 1995.

In a further embodiment of the invention the formulation further comprises a chelating agent. The use of a chelating agent in pharmaceutical compositions is well-known to the skilled person. For convenience reference is made to Remington: *The Science and Practice of Pharmacy*, $19^{th}$ edition, 1995.

In a further embodiment of the invention the formulation further comprises a stabilizer. The term "stabiliser" as used herein refers to chemicals added to polypeptide containing pharmaceutical formulations in order to stabilize the peptide, i.e. to increase the shelf life and/or in-use time of such formulations. The use of a stabilizer in pharmaceutical compositions is well-known to the skilled person. For convenience reference is made to Remington: *The Science and Practice of Pharmacy*, $19^{th}$ edition, 1995.

In a further embodiment of the invention the formulation further comprises a surfactant. The term "surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general. The use of a surfactant in pharmaceutical compositions is well-known to the skilled person. For convenience reference is made to Remington: *The Science and Practice of Pharmacy*, $19^{th}$ edition, 1995.

In a further embodiment of the invention the formulation further comprises protease inhibitors.

It is possible that other ingredients may be present in the insulin analogue pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an insulin analogue according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the insulin analogue compound, increase bioavailability, increase solubility, decrease adverse effects, achieve chronotherapy well known to those skilled in the art, and increase patient compliance or any combination thereof.

Compositions of the current invention are useful in the formulation of solids, semisolids, powder and solutions for pulmonary administration of insulin analogue, using, for example a metered dose inhaler, dry powder inhaler and a nebulizer, all being devices well known to those skilled in the art.

Compositions of the current invention may be useful in the formulation of controlled, sustained, protracting, retarded, and slow release drug delivery systems. More specifically, but not limited to, compositions may be useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles.

Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and super-critical fluid processes. General reference is made to Handbook of Pharmaceutical Controlled Release (Wise, D. L., ed. Marcel Dekker, N.Y., 2000) and Drug and the Pharmaceutical Sciences vol. 99: Protein Formulation and Delivery (Mac-Nally, E. J., ed. Marcel Dekker, N.Y., 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the insulin analogue compound in the form of a nasal or pulmonal spray. As a still further option, the pharmaceutical compositions containing the insulin analogue compound of the invention can also be adapted to transdermal administration, e.g. by needle-free injection or from a patch, optionally an iontophoretic patch, or transmucosal, e.g. buccal, administration.

The insulin analogue according to the invention can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

In a further embodiment, the formulation could be aerosolized by any known aerosolisation technology, such as nebulisation, to achieve a MMAD of aerosol particles less than 10 µm, more preferably between 1-5 µm, and most preferably between 1-3 µm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the insulin analogue compound may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the insulin analogue compound is stable for more than 6 weeks of usage and for more than 3 years of storage.

In another embodiment of the invention the pharmaceutical formulation comprising the insulin analogue compound is stable for more than 4 weeks of usage and for more than 3 years of storage.

In a further embodiment of the invention the pharmaceutical formulation comprising the insulin analogue compound is stable for more than 4 weeks of usage and for more than two years of storage.

In an even further embodiment of the invention the pharmaceutical formulation comprising the insulin analogue compound is stable for more than 2 weeks of usage and for more than two years of storage.

Aqueous suspensions may contain the active compounds in admixture with excipients suitable for the manufacture of aqueous suspensions.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These formulations may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical formulations comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent.

In a further embodiment of the invention, the formulation further comprises a permeation enhancer. Bile salts and fatty acids are most often considered to increase the oral permeability of the lipid bi-layer membranes of the epithelial cell lining of the GI tract. In general, permeation enhancers increase paracellular and trancellular transport of macromolecules by reversible altering the membrane integrity. The bile salt is selected from the group consisting of cholate, deoxycholate, taurocholate, glycocholate, taurodeoxycholate, ursodeoxycholate, tauroursodeoxycholate, and chenodeoxycholate. The fatty acids is selected from the group of short, medium and long chain fatty acids, such as caprylic acid, capric acid, lauric acid, myristic acid, plamitic acid, stearic acid etc. Others enhancers could be surfactants such as monoglycerides, polyoxyethylene esters, sorbitan surfactants (noninic) and sulphates (anionic).

In a further embodiment of the invention, the formulation further comprises a mucoadhesive polymer. An intimate contact of the drug delivery system to the mucosa of the gastrointestinal tract can be obtained by use of such a mucoadhesive polymer. An intimate contact of the dosage form to the membrane seems advantageous as an enzymatic degradation of the therapeutically active polypeptide on the way between the delivery system and the absorption membrane can be avoided. Moreover, a step concentration gradient on the absorption membrane representing the driving force for passive drug uptake can be provided.

In a further embodiment of the invention, the formulation further comprises an inhibitor of a proteolytic enzyme(s) to further circumvent the enzymatic barrier and achieving the delivery of the therapeutically active polypeptide such as aminopeptidase inhibitor, amastatin, bestatin, boroleucine and puromycin. Examples of protease inhibitors are sodium glycolate, camostat mesilate, bacitracin, soybean trypsin inhibitor and aprotinin.

Entrapment and encapsulation is a technique used in drug delivery systems for therapeutically active polypeptides to optimize delivery properties including protection against enzymatic degradation. Entrapment or encapsulation could be in the form of polymeric drug delivery systems such as hydrogels and nanocapsules/microspheres, and lipid drug delivery systems such as liposomes and micro emulsions.

Formulations of the current invention may be administered in several dosage forms, for example, as solutions, suspensions, micro- and nano suspension, emulsions, microemulsions, multiple emulsion, foams, salves, pastes, ointments, tablets, coated tablets, effervescent tablets, sublingual tablets, buccal tablets, capsules, for example, hard gelatine capsules and soft gelatine capsules, powder, granules, in situ transforming solutions, for example in situ gelling, in situ setting, in situ precipitating, in situ crystallization, stomach floating formulation such as floating suspension, floating tablet or the like.

In another embodiment, the present invention relates to an insulin analogue according to the invention for use as a medicament.

In one embodiment, an insulin analogue according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, stroke, coronary heart disease and other cardiovascular disorders, inflammatory bowel syndrome, dyspepsia and gastric ulcers.

In another embodiment, an insulin analogue according to the invention is used as a medicament for delaying or preventing disease progression in type 2 diabetes.

In another embodiment, an insulin analogue according to the invention is used as a medicament for decreasing food intake, decreasing β-cell apoptosis, increasing β-cell function and β-cell mass, and/or for restoring glucose sensitivity to β-cells.

In one embodiment of the invention, the derivative according to the invention is for use as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers or for delaying or preventing disease progression in type 2 diabetes or for decreasing food intake, decreasing β-cell apoptosis, increasing β-cell function and β-cell mass, and/or for restoring glucose sensitivity to β-cells, is provided.

In a further embodiment of the invention, a method for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers or for delaying or preventing disease progression in type 2 diabetes or for decreasing food intake, decreasing β-cell apoptosis, increasing β-cell function and β-cell mass, and/or for restoring glucose sensitivity to β-cells, the method comprising administering to a patient in need of such treatment an effective amount for such treatment of an insulin analogue according to the invention, is provided.

The treatment with an insulin analogue according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: GLP-1 and GLP-1 derivatives and analogues, GLP-2 and GLP-2 derivatives and analogues, Exendin-4 and Exendin-4 derivatives and analogues, amylin and amylin derivatives and analogues, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins) compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, 3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TRβ agonists; histamine H3 antagonists, gastrin and gastrin analogues and derivatives.

It should be understood that any suitable combination of the derivatives according to the invention with one or more of the above-mentioned compounds and optionally one or more further pharmacologically active substances are considered to be within the scope of the present invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLE

Example 1

Comparison of Proteolytic Stability (Half-Life) of B25H, A14E, A14E_B25H and Human Insulin Towards Pepsin, Chymotrypsin, and Carboxypeptidase A Proteolytic stability of human insulin and insulin analogues (0.06 mM, 10 μL) towards chymotrypsin or pepsin (0.34-3.4 μg) was measured after incubation in 100 mM $NH_4HCO_3$, pH 8.1 or 10 mM HCl, pH 2.0, respectively and 25° C. at a final volume of 100 μL. At various times (0, 5, 15, 30 and 60 min) samples were quenched with an equal volume of 0.5%TFA or 0.1 M TrisHCl, pH 8.0 (final pH 7.7) and transferred to 5° C. Human insulin and insulin analogues were immediately analyzed by RP-HPLC at 214 nm and the area under the peak corresponding to intact protein was determined.

Stability of human insulin and insulin analogues (0.06 mM, 13.9 μg) towards carboxypeptidase A (6.8 μL of working solution, 20 mg/ml, 53 units/mg, Sigma C-9268) was measured after incubation in 5 mM NaP,140 mM NaCl, 70 ppm Tween20, pH 7.4 and 37° C. at a final volume of 400 μL. At various times (5, 15, 30, 60 min) samples were quenched with an equal volume of 0.2% TFA and transferred to 5° C. Reference samples (0 min) were prepared without adding enzymes. Human insulin and analogues were immediately analyzed by RP-HPLC in a neutral buffer system at 214 nm and the area under the peak corresponding to intact protein was determined. Identical retention times were observed for human insulin and desB30. Half-lives ($T_{1/2}$) were obtained from the curves and the fold increase/decrease compared to human insulin was calculated (Stability relative fold). Similar half-lives were determined for human insulin, $T_{1/2}$=6.9 min, and desB30 human insulin, $T_{1/2}$=6.7.

| Mutation Site(s) in Human Insulin | $T_{1/2}$ [Min] (Fold) Pepsin | $T_{1/2}$ (Min)/Fold Chymotrypsin | $T_{1/2}$ (Min)/Fold Carboxypeptidase A |
|---|---|---|---|
| B25H | 17.8 (16.2) | 25.7 (5.1) | 25.7 (2.1) |
| None | 1.1 (1.0) | 5.0 (1.0) | 6.9 (1.0) |
| A14E, DESB30 | 3.7 (3.4) | 33.2 (6.6) | 15.7 (2.3) |
| None | 1.1 (1.0) | 5.0 (1.0) | 6.9 (1.0) |
| A14E, B25H, DESB30 | 42.4 (38.5) | 62.4 (12.5) | 61.9 (9.0) |
| None | 1.1 (1.0) | 5.0 (1.0) | 6.9 (1.0) |

Example 2

Identification of Protease Cleavage Sites within Insulin by MS Analysis and Enzyme Specificity Identification of protease cleavage sites were carried out by time course analysis of limited proteolysis of insulin and insulin analogues by various enzymes (pepsin, chymotrypsin, carboxypeptidase A) by LC-MS. Generated peptide fragments were identified by MS or MS/MS and quantified at 214 nm in order to identify minor and major cleavage sites (hot-spots). The following hot-spots for pepsin (B24-25, B25-26, B26-27) and chymotrypsin (B16-17, B24-25, B25-26, B26-27, A14-15 and A19-20) within human insulin were identified. Interestingly, the hot-spots overlap with insulin-degrading enzyme (IDE), see below, and cathepsin D (Hanne Refsgaard, Novo Nordisk A/S, personal communication).

Cleavage sites within the insulin sequence was also predicted based on enzyme specificity of chymotrypsin, trypsin and insulin-degrading enzyme (IDE) as shown below in example 3. The predicted cleavage sites for trypsin (basic residues, C-term. to Lys, Arg), elastase (aliphatic residues, C-term. to Ala, Val, Gly, Ser), carboxypeptidase A (broad specificity, but not Arg, Lys & Pro), pepsin A (aromatic residues, N-term. to Trp, Tyr, Phe, and Leu and various other residues), and chymotrypsin (aromatic residues, C-term. to Trp, Tyr, Phe, and Leu, but not Xxx-Pro) are described in several hand-books of biochemistry. Cleavage sites for IDE within insulin has recently been published: B9-10, B10-11, B13-14, B14-15, B24-25, B25-26, A13-14, A14-15 (Duckworth et al., 2006) and the following substitutions have been shown to inhibit IDE degradation of insulin: B10D and B4E_B16Q_B17F (Bennett et al., 2003).

Example 3

Repeated Cycles of Hot-Spot Identification within A14E, B25H, desB30 Human Insulin Major hot-spots for chymotrypsin cleavage (B16-17, B24-25, A19-20) and minor cleavage sites (B1-2, B6-7),were identified in A14E, B25H, desB30 human insulin according to the method described in example 2. Insulin analogues were designed based on the identified cleavage sites and predicted cleavage sites from the enzyme specificity. Amino acid residues for substitution were selected in order to remove the cleavage sites and to increase the solubility.

Chymotrypsin, Analogue Design Based on Hot-Spots Identified by LC-MS of Digests of A14E, B25H, desB30 Human Insulin:

A14X1 B25H desB30X12 HI B1X2 B6X3 B16X6 B24X8 A19X11
X1=E/D/H/Q/N/S/T/M/P
X2=E/D/H/Q/N/S/T/M/P/native aa
X3=E/D/H/Q/N/S/T/M/P/native aa
X6=E/D/H/Q/N/S/T/M/P/native aa
X8=E/D/H/Q/N/S/T/M/P/native aa
X11=E/D/H/Q/N/S/T/M/P/native aa
X12=desB30/native aa
Note: substitution of B24 and/or A19 in human insulin is likely to significantly reduce receptor affinity.

A14X1 B25P desB30X12 HI B1X2 B6X3 B16X6 B24X8 A19X11
X1=E/D/H/Q/N/S/T/M/P
X2=E/D/H/Q/N/S/T/M/P/native aa
X3=E/D/H/Q/N/S/T/M/P/native aa
X6=E/D/H/Q/N/S/T/M/P/native aa
X8=E/D/H/Q/N/S/T/M/P/native aa
X11=E/D/H/Q/N/S/T/M/P/native aa
X12=desB30/native aa Note: substitution of B25 with Pro is likely to significantly reduce chymotrypsin cleavage at B24-25.

Chymotrypsin, Design Based on Identified and Predicted Hot-Spots:

A14X1 B25H desB30X12 HI B1X2 B6X3 B11X4 B15X5 B16X6 B17X7 B24X8 A13X9 A16X10 A19X11

X1=E/D/H/Q/N/S/T/M/P
X2=E/D/H/Q/N/S/T/M/P/native aa
X3=E/D/H/Q/N/S/T/M/P/native aa
X4=E/D/H/Q/N/S/T/M/P/native aa
X5=E/D/H/Q/N/S/T/M/P/native aa
X6=E/D/H/Q/N/S/T/M/P/native aa
X7=E/D/H/Q/N/S/T/M/P/native aa
X8=E/D/H/Q/N/S/T/M/P/native aa
X9=E/D/H/Q/N/S/T/M/P/native aa
X10=E/D/H/Q/N/S/T/M/P/native aa
X11=E/D/H/Q/N/S/T/M/P/native aa
X12=desB30/native aa Note: substitution of B11, B15, B24, A13, A16, and/or A19 in human insulin is likely to significantly reduce receptor affinity.

Chymotrypsin+Trypsin, Design Based on Identified and Predicted Hot-Spots:

A14X1 B25H desB30X12 HI B1X2 B6X3 B11X4 B15X5 B16X6 B17X7 B24X8 A13X9 A16X10 A19X11 B22X13

X1=E/D/H/Q/N/S/T/M/P

X2=E/D/H/Q/N/S/T/M/P/native aa

X3=E/D/H/Q/N/S/T/M/P/native aa

X4=E/D/H/Q/N/S/T/M/P/native aa

X5=E/D/H/Q/N/S/T/M/P/native aa

X6=E/D/H/Q/N/S/T/M/P/native aa

X7=E/D/H/Q/N/S/T/M/P/native aa

X8=E/D/H/Q/N/S/T/M/P/native aa

X9=E/D/H/Q/N/S/T/M/P/native aa

X10=E/D/H/Q/N/S/T/M/P/native aa

X11=E/D/H/Q/N/S/T/M/P/native aa

X12=desB30/native aa

X13=E/D/H/Q/N/S/T/M/P/native aa

Chymotrypsin+Trypsin+Insulin-Degrading Enzyme (IDE), Design Based on Identified and Predicted Hot-Spots:

A14X1 B25H desB30X12 HI B1X2 B6X3 B11X4 B15X5 B16X6 B17X7 B24X8 A13X9 A16X10 A19X11 B22X13 B4X14 B9X15 B10X16 B13X17 B14X18

X1=E/D/H/Q/N/S/T/M/P

X2=E/D/H/Q/N/S/T/M/P/native aa

X3=E/D/H/Q/N/S/T/M/P/native aa

X4=E/D/H/Q/N/S/T/M/P/native aa

X5=E/D/H/Q/N/S/T/M/P/native aa

X6=E/D/H/Q/N/S/T/M/P/native aa

X7=E/D/H/Q/N/S/T/M/P/native aa

X8=E/D/H/Q/N/S/T/M/P/native aa

X9=E/D/H/Q/N/S/T/M/P/native aa

X10=E/D/H/Q/N/S/T/M/P/native aa

X11=E/D/H/Q/N/S/T/M/P/native aa

X12=desB30/native aa

X13=E/D/H/Q/N/S/T/M/P/native aa

X14=E/D/H/Q/N/S/T/M/P/native aa

X15=E/D/H/Q/N/S/T/M/P/native aa

X16=E/D/H/Q/N/S/T/M/P/native aa

X17=E/D/H/Q/N/S/T/M/P/native aa

X18=E/D/H/Q/N/S/T/M/P/native aa

Example 4

Proteolytic Stability (Half-Life) of Insulin Analogues Towards Chymotrypsin

Insulin analogues were tested in stability assays and analogues exhibiting enhanced resistance to proteolytic digestion were identified by increased half-lives according to the methods described in example 1. The results demonstrate the potential of the further improved insulin analogues for increased bioavailability due to enhanced resistance to proteolytical degradation and improved solubility.

The stability of the following insulin analogues towards chymotrypsin have been tested relatively to human insulin:

| Insulin analogues | Chymotrypsin digestion [Fold stability relative to Human Insulin] |
|---|---|
| A14E, B25H, desB27, desB28, desB29, desB30 human insulin | 43.8 |
| A8H, A14E, B25H, B27E, desB30 human insulin | 38.9 |
| EEAEAEAPK-B(1-29)-B25H-AAK-A(1-21)-A14E human insulin | 33.2 |
| A8H, A14E, B1E, B25H, B27E, desB30 human insulin | 22.8 |
| A14E, B25H, B28D, desB30 human insulin | 17.4 |
| A14E, B25H, B26D, desB30 human insulin | 16.6 |
| A14E, B25H, B27E, desB30 human insulin | 14.1 |
| A8H, A14E, B25H, desB30 human insulin | 13.3 |
| A8H, A14E, B10E, B25H, desB30 human insulin | 12.6 |
| A14E, B25H, desB30 human insulin | 12.5 |
| A14E, B1E, B25H, B27E, desB30 human insulin | 11.9 |
| A8H, A14E, B1E, B25H, desB30 human insulin | 10.2 |
| A8H, A14E, B1E, B16E, B25H, B27E, desB30 human insulin | 8.3 |
| A14D, B25H, desB30 human insulin | 7.9 |
| A14E, B27E, desB30 human insulin | 7.7 |
| A14E, B28D, desB30 human insulin | 7.5 |
| A8H, B10D, B25H human insulin | 7.4 |
| A14E, B1E, B16E, B25H, B27E, desB30 human insulin | 5.5 |
| A14E, B1E, B25H, desB30 human insulin | 4.8 |
| A14H, B25H, desB30 human insulin | 4.5 |
| A14E, B25H human insulin | 4.1 |
| A14E, B1E, B27E, desB30 human insulin | 3.9 |
| A8H, A14E, B16E, B25H, desB30 human insulin | 2.3 |
| A14E, B16E, B25H, desB30 human insulin | 2.1 |
| human insulin (reference) | 1 |

Example 5

Proteolytic Stability of Insulin Analogues Towards Extracts from Rat Intestine (Duodenum Lumen)

Insulin analogues were tested for their stability towards proteolytic degradation in intestinal extracts. The extracts were prepared by washing the lumenal content of fasted animals. Insulin analogues were incubated with diluted extracts at 37° C. at pH=7.4 and after 20 h incubation the concentration of the intact compound was determined by RP-HPLC. The relative amounts of intact insulin analogues and intact human insulin were compared. Approximately 5-10 fold difference in the stability between human insulin and the analogue A14E B25H desB30 human insulin was found.

The invention claimed is:

1. An analogue of human insulin wherein in said analogue at least two hydrophobic amino acids of the parent human insulin have been substituted with hydrophilic amino acids, wherein i) at least one substitution is at one of amino acids A13 or A14 of the parent human insulin and at least one substitution is at one of amino acids B24, B25 or B26 of the parent human insulin, and ii) such human insulin analogue has less than a total of 8 modifications relative to the parent human insulin and the amino acid at position A21 of the A chain of the analogue is the C-terminal amino acid of said A chain and the amino acid at position B29 of the analogue is absent or is Lys.

2. The human insulin analogue according to claim 1 which shows increased stability towards one or more protease enzymes relative to the parent human insulin.

3. The human insulin analogue according to claim 1 comprising an A-chain amino acid sequence of formula (1):

Formula (1)

(SEQ ID No: 1)

$Xaa_{A(-2)}$-$Xaa_{A(-1)}$-$Xaa_{A0}$-Gly-Ile-Val-Glu-Gln-Cys-

Cys-$Xaa_{A8}$-Ser-Ile-Cys-$Xaa_{A12}$-$Xaa_{A13}$-$Xaa_{A14}$-$Xaa_{A15}$-

Leu-Glu-$Xaa_{A18}$-Tyr-Cys-$XaaA_{21}$-$Xaa_{22}$ and a B-chain amino acid sequence of formula (2):

Formula (2)

(SEQ ID No: 2)

$Xaa_{B(-2)}$-$Xaa_{B(-1)}$-$Xaa_{B0}$-$Xaa_{B1}$-$Xaa_{B2}$-$Xaa_{B3}$-$Xaa_{B4}$-

His-Leu-Cys-Gly-Ser-$Xaa_{B10}$-Leu-Val-Glu-Ala-Leu- $Xaa_{B16}$-Leu-Val-Cys-Gly-Glu-Arg-Gly-$Xaa_{B24}$-$Xaa_{B25}$-

$Xaa_{B26}$-$Xaa_{B27}$-$Xaa_{B28}$-$Xaa_{B29}$-$Xaa_{B30}$-$Xaa_{B31}$-$Xaa_{B32}$ wherein
  $Xaa_{A(-2)}$ is absent or Gly;
  $Xaa_{A(-1)}$ is absent or Pro;
  $Xaa_{A0}$ is absent or Pro;
  $Xaa_{A8}$ is independently selected from Thr and His;
  $Xaa_{A12}$ is independently selected from Ser, Asp and Glu;
  $Xaa_{A13}$ is independently selected from Leu, Thr, Asn, Asp, Gln, His, Lys, Gly, Arg, Pro, Ser and Glu;
  $Xaa_{A14}$ is independently selected from Tyr, Thr, Asn, Asp, Gln, His, Lys, Gly, Arg, Pro, Ser and Glu;
  $Xaa_{A15}$ is independently selected from Gln, Asp and Glu;
  $Xaa_{A18}$ is independently selected from Asn, Lys and Gln;
  $Xaa_{A21}$ is independently selected from Asn and Gln;
  $Xaa_{A22}$ is absent;
  $Xaa_{B(-2)}$ is absent or Gly;
  $Xaa_{B(-1)}$ is absent or Pro;
  $Xaa_{B(-1)}$ is absent or Pro;
  $Xaa_{B0}$ is absent or independently selected from Phe and Glu;
  $Xaa_{B2}$ is absent or Val;
  $Xaa_{B3}$ is absent or independently selected from Asn and Gln;
  $Xaa_{B4}$ is independently selected from Gln and Glu;
  $Xaa_{B10}$ is independently selected from His, Asp, Pro and Glu;
  $Xaa_{B16}$ is independently selected from Tyr, Asp, Gln, His, Arg, and Glu;
  $Xaa_{B24}$ is independently selected from Phe and His;
  $Xaa_{B25}$ is independently selected from Phe and His;
  $Xaa_{B26}$ is absent or independently selected from Tyr, His, Thr, Gly and Asp;
  $Xaa_{B27}$ is absent or independently selected from Thr, Asn, Asp, Gln, His, Lys, Gly, Arg, Pro, Ser and Glu;
  $Xaa_{B28}$ is absent or independently selected from Pro, His, Gly and Asp;
  $Xaa_{B29}$ is absent or Lys;
  $Xaa_{B30}$ is absent or Thr;
  $Xaa_{B31}$ is absent or Leu;
  $Xaa_{B32}$ is absent or Glu;
  the C-terminal may optionally be derivatized as an amide;
  wherein the A-chain amino acid sequence and the B-chain amino acid sequence are connected by disulphide bridges between the cysteine in position 7 of the A-chain and the cysteine in position 7 of the B-chain, and between the cysteine in position 20 of the A-chain and the cysteine in position 19 of the B-chain and wherein the cysteines in positions 6 and 11 of the A-chain are connected by a disulphide bridge;

wherein optionally the N-terminal A-chain amino acid sequence is connected to the C-terminal B-chain amino acid sequence by an amino acid sequence comprising 3-7 amino acids to form a single chain insulin molecule, wherein optionally the N-terminal of the B-chain is extended with 1-10 amino acids.

4. A pharmaceutical composition comprising a biologically active amount of the human insulin analogue according to claim 1 and a pharmaceutically acceptable carrier.

5. A method for treating hyperglycemia, type 2 diabetes, impaired glucose tolerance, type 1 diabetes, obesity, syndrome X or dyslipidemia in a subject, said method comprising administering to said subject a pharmaceutical composition according to claim 4.

6. The method according to claim 5 wherein said composition is administered to said subject via oral administration.

7. A nucleic acid sequence encoding the human insulin analogue of claim 1.

8. A process for preparing a pharmaceutical composition, said process comprising mixing the human insulin analogue according to claim 1 with pharmaceutically acceptable substances and/or excipients.

9. A method for decreasing food intake, decreasing β-cell apoptosis, increasing β-cell function and β-cell mass, and/or for restoring glucose sensitivity to β-cells in a subject, said method comprising administering to said subject a pharmaceutical composition according to claim 4.

10. The human insulin analogue according to claim 1, wherein the amino acid in position A12 is Glu or Asp and/or the amino acid in position A13 is His, Asn, Glu or Asp and/or the amino acid in position A14 is Asn, Gln, Glu, Arg, Asp, Gly or His and/or the amino acid in position A15 is Glu or Asp; and the amino acid in position B24 is His and/or the amino acid in position B25 is His and/or the amino acid in position B26 is His, Gly, Asp or Thr.

11. The human insulin analogue according to claim 10, wherein the amino acid in position A14 is Glu, Asp or His, and the amino acid in position B25 is His.

12. The human insulin analogue according to claim 11, wherein the amino acid in position A14 is Glu, Asp or His, and the amino acid in position B25 is His and the amino acid in position B30 is deleted.

13. A pharmaceutical composition comprising a biologically active amount of the human insulin analogue according to claim 10 and a pharmaceutically acceptable carrier.

14. An insulin analogue selected from the group consisting of:
  A14E, B25H, desB30 human insulin;
  A14H, B25H, desB30 human insulin;
  A14E, B1E, B25H, desB30 human insulin;
  A14E, B16E, B25H, desB30 human insulin;
  A14E, B25H, B28D, desB30 human insulin;
  A14E, B25H, B27E, desB30 human insulin;
  A14E, B1E, B25H, B27E, desB30 human insulin;
  A14E, B1E, B16E, B25H, B27E, desB30 human insulin;
  A8H, A14E, B25H, desB30 human insulin;
  A8H, A14E, B25H, B27E, desB30 human insulin;
  A8H, A14E, B1E, B25H, desB30 human insulin;
  A8H, A14E, B1E, B25H, B27E, desB30 human insulin;
  A8H, A14E, B1E, B16E, B25H, B27E, desB30 human insulin;
  A8H, A14E, B16E, B25H, desB30 human insulin;
  A14E, B25H, B26D, desB30 human insulin;
  A14E, B1E, B27E, desB30 human insulin;
  A14E, B27E, desB30 human insulin;
  A14E, B28D, desB30 human insulin;
  A14D, B25H, desB30 human insulin;

A(-1)P, A(0)P, A14E, B25H, desB30 human insulin;
A14E, B(-1)P, B(0)P, B25H, desB30 human insulin;
A(-1)P, A(0)P, A14E, B(-1)P, B(0)P, B25H, desB30 human insulin;
A14E, B25H, B30T, B31L, B32E human insulin;
A14E, B25H human insulin;
A14E, B16H, B25H, desB30 human insulin;
A14E, B10P, B25H, desB30 human insulin;
A14E, B10E, B25H, desB30 human insulin;
A14E, B4E, B25H, desB30 human insulin;
A14H, B16H, B25H, desB30 human insulin;
A14H, B10E, B25H, desB30 human insulin;
A14E, B25H, desB27, desB28, desB29, desB30 human insulin;
A13H, A14E, B10E, B25H, desB30 human insulin;
A13H, A14E, B25H, desB30 human insulin;
A14E, A18Q, B3Q, B2H, desB30 human insulin;
A14E, B24H, B25H, desB30 human insulin;
A8H, A14E, B10D, B25H, B26G, desB27, desB28, desB29, desB30 human insulin;
A8H, A14E, B10D, B25H-amide, desB26, desB27, desB28, desB29, desB30 human insulin;
A14E, B25H, desB26, desB27, desB28, desB29, desB30 human insulin;
A14E, B25H, B26G, desB27, desB28, desB29, desB30 human insulin;
A14E, B25H-amide, desB27, desB28, desB29, desB30 human insulin
A14E, B25H, B26G, B27G, B28G, desB30 human insulin;
A14E, B26G, desB27, desB28, desB29, desB30 human insulin;
A14E, B25H, desB26, desB27, desB28, desB29, desB30 human insulin;
A14E, A18Q, A21Q, B3Q, B25H, desB30 human insulin;
A14E, A18Q, A21Q, B3Q, B25H, B27E, desB30 human insulin;
A14E, A18Q, B3Q, B25H, desB30 human insulin;
A13H, A14E, B1E, B25H, desB30 human insulin;
A13N, A14E, B25H, desB30 human insulin;
A13N, A14E, B1E, B25H, desB30 human insulin;
A(-2)G, A(-1)P, A(0)P, A14E, B25H, desB30 human insulin;
A14E, B(-2)G, B(-1)P, B(0)P, B25H, desB30 human insulin;
A(-2)G, A(-1)P, A(0)P, A14E, B(-2)G, B(-1)P, B(0)P, B25H, desB30 human insulin;
A14E, B27R, B28D, B29K, desB30 human insulin;
A14E, B25H, B27R, B28D, B29K, desB30 human insulin;
A14E, B25H, B26T, B27R, B28D, B29K, desB30 human insulin;
A14E, A18K, B25H, desB27, desB28, desB29, desB30 human insulin;
A14E, desB1, desB2, desB3, B25H-amide, desB26, desB27, desB28, desB29, desB30 human insulin;
A14E, desB1, desB2, desB3, B25H, desB27, desB28, desB29, desB30 human insulin;
A14E, desB1, desB2, desB3, B16H, B25H, desB27, desB28, desB29, desB30 human insulin;
A14E, B25H, B27R, desB30 human insulin;
A14E, B25H, B27H, desB30 human insulin;
A14E, B25H, B27R, desB28-B30 human insulin;
A14E, B25H, B27H, desB28-B30 human insulin;
A14E, B25H, B27E, desB28-B30 human insulin;
A14E, B25H, B27K, desB28-B30 human insulin;
A14E, B27K, desB28-B30 human insulin;
A14E, A18Q, B3Q, B25H, desB30 human insulin;
A13E, A14E, B25H, desB30 human insulin;
A12E, A14E, B25H, desB30 human insulin;
A15E, A14E, B25H, desB30 human insulin;
A13E, B25H, desB30 human insulin;
A12E, B25H, desB30 human insulin;
A15E, B25H, desB30 human insulin;
A14E, B25H, desB27, desB30 human insulin;
A14E, B25H, B26D, B27E, desB30 human insulin;
EEAEAEAPK (SEQ ID NO: 5)-B(1-29)-B25H-AAK-A(1-21)-A14E human insulin;
EEAEPK (SEQ ID NO: 6)-B(1-29)-B25H-DGK-A(1-21)-A14E human insulin;
B(1-29)-B25H-AAK-A(1-21)-A14E human insulin;
B(1-29)-B1E, B25H-AAK-A(1-21)-A14E human insulin;
B(1-29)-B25H, B27E-AAK-A(1-21)-ABH, A14E human insulin;
B(1-29)-B1E, B25H, B27E-AAK-A(1-21).A8H, A14E human insulin;
EEAEAEAPK (SEQ ID NO: 5)-B(1-29)-B16E, B25H-AAK-A(1-21)-A8H. A14E human insulin;
B(1-29)-B25H, B29Q-TGLGGGQ (SEQ ID NO: 7)-A(1-21)-A14E human insulin;
B(1-29)-B16E, B25H, B29Q-TGLGGGQ (SEQ ID NO: 7)-A(1-21)-A14E human insulin;
B(1-29)-B25H, B29Q-TGLGGGQ (SEQ ID NO: 7)-A(1-21)-A8H, A14E human insulin; A14E, B25H, B27R, desB30 human insulin;
A14E, B25H, B27N, desB30 human insulin;
A14E, B25H, B27D, desB30 human insulin;
A14E, B25H, B27Q, desB30 human insulin;
A14E, B25H, B27E, desB30 human insulin;
A14E, B25H, B27G, desB30 human insulin;
A14E, B25H, B27H, desB30 human insulin;
A14E, B25H, B27K, desB30 human insulin;
A14E, B25H, B27P, desB30 human insulin;
A14E, B25H, B27S, desB30 human insulin;
A14E, B25H, B27T, desB30 human insulin;
A13R, A14E, B25H, desB30 human insulin;
A13N, A14E, B25H, desB30 human insulin;
A13D, A14E, B25H, desB30 human insulin;
A13Q, A14E, B25H, desB30 human insulin;
A13E, A14E, B25H, desB30 human insulin;
A13G, A14E, B25H, desB30 human insulin;
A13H, A14E, B25H, desB30 human insulin;
A13K, A14E, B25H, desB30 human insulin;
A13P, A14E, B25H, desB30 human insulin;
A13S, A14E, B25H, desB30 human insulin;
A13T, A14E, B25H, desB30 human insulin;
A14E, B16R, B25H, desB30 human insulin;
A14E, B16D, B25H, desB30 human insulin;
A14E, B16Q, B25H, desB30 human insulin;
A14E, B16E, B25H, desB30 human insulin;
A14E, B16H, B25H, desB30 human insulin;
A14R, B25H, desB30 human insulin;
A14N, B25H, desB30 human insulin;
A14D, B25H, desB30 human insulin;
A14Q, B25H, desB30 human insulin;
A14E, B25H, desB30 human insulin;
A14G, B25H, desB30 human insulin;
A14H, B25H, desB30 human insulin;
A8H, B10D, B25H human insulin; and
A8H, A14E, B10E, B25H, desB30 human insulin.

15. A pharmaceutical composition comprising a biologically active amount of the human insulin analogue according to claim 14 and a pharmaceutically acceptable carrier.

16. The human insulin analogue according to claim 1, wherein such human insulin analogue has less than 7 modifications relative to the parent human insulin.

17. The human insulin analogue according to claim 1, wherein such human insulin analogue has less than 6 modifications relative to the parent human insulin.

18. The human insulin analogue according to claim 1, wherein such human insulin analogue has less than 5 modifications relative to the parent human insulin.

19. The human insulin analogue according to claim 1, wherein such human insulin analogue has less than 4 modifications relative to the parent human insulin.

20. The human insulin analogue according to claim 1, wherein in i) at least one substitution is at one of amino acids A13 or A14 of the parent human insulin and at least one substitution is at one of amino acids B24 or B25 of the parent human insulin.

21. The human insulin analogue according to claim 1, wherein in i) at least one substitution is at one of amino acids A13 or A14 of the parent human insulin and at least one substitution is at one of amino acids B25 or B26 of the parent human insulin.

22. The human insulin analogue according to claim 1, wherein in i) at least one substitution is at amino acid A14 of the parent human insulin and at least one substitution is at one of amino acids B24 or B25 of the parent human insulin.

23. The human insulin analogue according to claim 1, wherein in i) at least one substitution is at amino acid A14 of the parent human insulin and at least one substitution is at one of amino acids B25 or B26 of the parent human insulin.

24. The human insulin analogue according to claim 1, wherein B25 is substituted with a hydrophilic amino acid.

25. The human insulin analogue according to claim 1, wherein B27 is absent.

26. The human insulin analogue according to claim 24, wherein B27 is absent.

27. The human insulin analogue according to claim 1, wherein B25 is substituted with a His.

28. The human insulin analogue according to claim 27, wherein B27 is absent.

29. The human insulin analogue according to claim 3, wherein $Xaa_{B27}$ is absent.

30. The human insulin analogue according to claim 3, wherein $Xaa_{B25}$ is His.

31. The human insulin analogue according to claim 3, wherein $Xaa_{B25}$ is His and $Xaa_{B27}$ is absent.

* * * * *

UNITED STATES PATENT AND TRADEMARK OFFICE
CERTIFICATE OF CORRECTION

| | | |
|---|---|---|
| PATENT NO. | : 9,018,161 B2 | Page 1 of 1 |
| APPLICATION NO. | : 12/442190 | |
| DATED | : April 28, 2015 | |
| INVENTOR(S) | : Peter K. Nielsen et al. | |

It is certified that error appears in the above-identified patent and that said Letters Patent is hereby corrected as shown below:

In the Claims

In claim 3, column 43, line 36, please replace with the following:

--$Xaa_{(\beta 0)}$ is absent or Pro;--

In claim 3, column 43, line 37, please replace with the following:

--$Xaa_{(\beta 1)}$ is absent or independently selected from Phe or Glu;--

In claim 14, column 45, line 17, please replace with the following:

--A14E, A18Q, B3Q, B25H, desB30 human insulin;--

In claim 14, column 46, line 14, please replace with the following:

--B(1-29)-B25H, B27E-AAK-A(1-21)-A8H, A14E human insulin;--

In claim 14, column 46, after line 26, please insert the following:

--A14E, B25H, B27R, desB30 human insulin;--

Signed and Sealed this
Sixth Day of October, 2015

Michelle K. Lee
*Director of the United States Patent and Trademark Office*

SEQUENCE LISTING

<160> NUMBER OF SEQ ID NOS: 7

<210> SEQ ID NO 1
<211> LENGTH: 25
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or Gly
<220> FEATURE:
<221> NAME/KEY: MISC_FEATURE
<222> LOCATION: (2)..(2)
<223> OTHER INFORMATION: Xaa is absent or Pro
<220> FEATURE:
<221> NAME/KEY: MISC_FEATURE
<222> LOCATION: (3)..(3)
<223> OTHER INFORMATION: Xaa is absent or Pro
<220> FEATURE:
<221> NAME/KEY: MISC_FEATURE
<222> LOCATION: (11)..(11)
<223> OTHER INFORMATION: Xaa is Thr or His
<220> FEATURE:
<221> NAME/KEY: MISC_FEATURE
<222> LOCATION: (15)..(15)
<223> OTHER INFORMATION: Xaa is Ser, Asp or Glu
<220> FEATURE:
<221> NAME/KEY: MISC_FEATURE
<222> LOCATION: (16)..(16)
<223> OTHER INFORMATION: Xaa is Leu, Thr, Asn, Asp, Gln, His, Lys, Gly,
      Arg, Pro, Ser or Glu
<220> FEATURE:
<221> NAME/KEY: MISC_FEATURE
<222> LOCATION: (17)..(17)
<223> OTHER INFORMATION: Xaa is Tyr, Thr, Asn, Asp, Gln, His, Lys, Gly,
      Arg, Pro, Ser or Glu
<220> FEATURE:
<221> NAME/KEY: MISC_FEATURE
<222> LOCATION: (18)..(18)
<223> OTHER INFORMATION: Xaa is Gln, Asp or Glu
<220> FEATURE:
<221> NAME/KEY: MISC_FEATURE
<222> LOCATION: (21)..(21)
<223> OTHER INFORMATION: Xaa is Asn, Lys or Gln
<220> FEATURE:
<221> NAME/KEY: MISC_FEATURE
<222> LOCATION: (24)..(24)
<223> OTHER INFORMATION: Xaa is Asn or Gln
<220> FEATURE:
<221> NAME/KEY: MISC_FEATURE
<222> LOCATION: (25)..(25)
<223> OTHER INFORMATION: Xaa is absent or Lys

<400> SEQUENCE: 1

Xaa Xaa Xaa Gly Ile Val Glu Gln Cys Cys Xaa Ser Ile Cys Xaa Xaa
1               5                   10                  15

Xaa Xaa Leu Glu Xaa Tyr Cys Xaa Xaa
            20                  25

<210> SEQ ID NO 2
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or Gly
<220> FEATURE:
<221> NAME/KEY: MISC_FEATURE

```
<222> LOCATION: (2)..(2)
<223> OTHER INFORMATION: Xaa is absent or Pro
<220> FEATURE:
<221> NAME/KEY: MISC_FEATURE
<222> LOCATION: (3)..(3)
<223> OTHER INFORMATION: Xaa is absent or Pro
<220> FEATURE:
<221> NAME/KEY: MISC_FEATURE
<222> LOCATION: (4)..(4)
<223> OTHER INFORMATION: Xaa is absent Phe or Glu
<220> FEATURE:
<221> NAME/KEY: MISC_FEATURE
<222> LOCATION: (5)..(5)
<223> OTHER INFORMATION: Xaa is absent or Val
<220> FEATURE:
<221> NAME/KEY: MISC_FEATURE
<222> LOCATION: (6)..(6)
<223> OTHER INFORMATION: Xaa is absent, Asn or Gln
<220> FEATURE:
<221> NAME/KEY: MISC_FEATURE
<222> LOCATION: (7)..(7)
<223> OTHER INFORMATION: Xaa is Gln or Glu
<220> FEATURE:
<221> NAME/KEY: MISC_FEATURE
<222> LOCATION: (13)..(13)
<223> OTHER INFORMATION: Xaa is His, Asp, Pro or Glu
<220> FEATURE:
<221> NAME/KEY: MISC_FEATURE
<222> LOCATION: (19)..(19)
<223> OTHER INFORMATION: Xaa is Tyr, Asp, Gln, His, Arg or Glu
<220> FEATURE:
<221> NAME/KEY: MISC_FEATURE
<222> LOCATION: (27)..(27)
<223> OTHER INFORMATION: Xaa is Phe or His
<220> FEATURE:
<221> NAME/KEY: MISC_FEATURE
<222> LOCATION: (28)..(28)
<223> OTHER INFORMATION: Xaa is Phe or His
<220> FEATURE:
<221> NAME/KEY: MISC_FEATURE
<222> LOCATION: (29)..(29)
<223> OTHER INFORMATION: Xaa is absent, Tyr, His, Thr, Gly or Asp
<220> FEATURE:
<221> NAME/KEY: MISC_FEATURE
<222> LOCATION: (30)..(30)
<223> OTHER INFORMATION: Xaa is absent, Thr, Asn, Asp, Gln, His, Lys,
      Gly, Arg, Pro, Ser or Glu
<220> FEATURE:
<221> NAME/KEY: MISC_FEATURE
<222> LOCATION: (31)..(31)
<223> OTHER INFORMATION: Xaa is absent, Pro, His, Gly or Asp
<220> FEATURE:
<221> NAME/KEY: MISC_FEATURE
<222> LOCATION: (32)..(32)
<223> OTHER INFORMATION: Xaa is absent, Lys or Gln
<220> FEATURE:
<221> NAME/KEY: MISC_FEATURE
<222> LOCATION: (33)..(33)
<223> OTHER INFORMATION: Xaa is absent or Thr
<220> FEATURE:
<221> NAME/KEY: MISC_FEATURE
<222> LOCATION: (34)..(34)
<223> OTHER INFORMATION: Xaa is absent or Leu
<220> FEATURE:
<221> NAME/KEY: MISC_FEATURE
<222> LOCATION: (35)..(35)
<223> OTHER INFORMATION: Xaa is absent or Glu

<400> SEQUENCE: 2

Xaa Xaa Xaa Xaa Xaa Xaa Xaa His Leu Cys Gly Ser Xaa Leu Val Glu
1               5                   10                  15

Ala Leu Xaa Leu Val Cys Gly Glu Arg Gly Xaa Xaa Xaa Xaa Xaa Xaa
                20                  25                  30

Xaa Xaa Xaa
        35
```

```
<210> SEQ ID NO 3
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Thr or His
<220> FEATURE:
<221> NAME/KEY: MISC_FEATURE
<222> LOCATION: (12)..(12)
<223> OTHER INFORMATION: Xaa is Ser, Asp or Glu
<220> FEATURE:
<221> NAME/KEY: MISC_FEATURE
<222> LOCATION: (13)..(13)
<223> OTHER INFORMATION: Xaa is Leu, Thr, Asn, Asp, Gln, His, Lys, Gly,
      Arg, Pro, Ser or Glu
<220> FEATURE:
<221> NAME/KEY: MISC_FEATURE
<222> LOCATION: (14)..(14)
<223> OTHER INFORMATION: Xaa is Thr, Asn, Asp, Gln, His, Lys, Gly, Arg,
      Pro, Ser or Glu
<220> FEATURE:
<221> NAME/KEY: MISC_FEATURE
<222> LOCATION: (15)..(15)
<223> OTHER INFORMATION: Xaa is Gln, Asp or Glu
<220> FEATURE:
<221> NAME/KEY: MISC_FEATURE
<222> LOCATION: (18)..(18)
<223> OTHER INFORMATION: Xaa is Asn, Lys or Gln
<220> FEATURE:
<221> NAME/KEY: MISC_FEATURE
<222> LOCATION: (21)..(21)
<223> OTHER INFORMATION: Xaa is Asn or Gln

<400> SEQUENCE: 3

Gly Ile Val Glu Gln Cys Cys Xaa Ser Ile Cys Xaa Xaa Xaa Xaa Leu
1               5                   10                  15

Glu Xaa Tyr Cys Xaa
            20

<210> SEQ ID NO 4
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Phe or Glu
<220> FEATURE:
<221> NAME/KEY: MISC_FEATURE
<222> LOCATION: (3)..(3)
<223> OTHER INFORMATION: Xaa is Asn or Gln
<220> FEATURE:
<221> NAME/KEY: MISC_FEATURE
<222> LOCATION: (4)..(4)
<223> OTHER INFORMATION: Xaa is Gln or Glu
<220> FEATURE:
<221> NAME/KEY: MISC_FEATURE
<222> LOCATION: (10)..(10)
<223> OTHER INFORMATION: Xaa is His, Asp, Pro or Glu
<220> FEATURE:
<221> NAME/KEY: MISC_FEATURE
<222> LOCATION: (16)..(16)
<223> OTHER INFORMATION: Xaa is Tyr, Asp, Gln, His, Arg or Glu
<220> FEATURE:
<221> NAME/KEY: MISC_FEATURE
<222> LOCATION: (24)..(24)
<223> OTHER INFORMATION: Xaa is Phe or His
<220> FEATURE:
<221> NAME/KEY: MISC_FEATURE
```

```
<222> LOCATION: (26)..(26)
<223> OTHER INFORMATION: Xaa is absent, Tyr, His, Thr, Gly or Asp
<220> FEATURE:
<221> NAME/KEY: MISC_FEATURE
<222> LOCATION: (27)..(27)
<223> OTHER INFORMATION: Xaa is absent, Thr, Asn, Asp, Gln, His, Lys,
      Gly, Arg, Pro, Ser or Glu
<220> FEATURE:
<221> NAME/KEY: MISC_FEATURE
<222> LOCATION: (28)..(28)
<223> OTHER INFORMATION: Xaa is absent, Pro, His, Gly or Asp
<220> FEATURE:
<221> NAME/KEY: MISC_FEATURE
<222> LOCATION: (29)..(29)
<223> OTHER INFORMATION: Xaa is absent, Lys or Gln
<220> FEATURE:
<221> NAME/KEY: MISC_FEATURE
<222> LOCATION: (30)..(30)
<223> OTHER INFORMATION: Xaa is absent or Thr

<400> SEQUENCE: 4

Xaa Val Xaa Xaa His Leu Cys Gly Ser Xaa Leu Val Glu Ala Leu Xaa
1               5                   10                  15

Leu Val Cys Gly Glu Arg Gly Xaa His Xaa Xaa Xaa Xaa Xaa
            20                  25                  30

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Glu Glu Ala Glu Ala Glu Ala Pro Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Glu Glu Ala Glu Pro Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Thr Gly Leu Gly Gly Gly Gln
1               5
```